United States Patent
Kaundinya et al.

(10) Patent No.: US 8,799,010 B2
(45) Date of Patent: Aug. 5, 2014

(54) TELEHEALTH SCHEDULING AND COMMUNICATIONS NETWORK

(75) Inventors: Murali P. Kaundinya, Bridgewater, NJ (US); John C. Santelli, Eden Prairie, MN (US); Christopher D. Clemens, Minneapolis, MN (US); Sorell B. Slaymaker, St. Paul, MN (US); Rahul Singh, Maple Grove, MN (US); Srinivas Kunani, Bakersfield, CA (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 100 days.

(21) Appl. No.: 12/437,479

(22) Filed: May 7, 2009
(Under 37 CFR 1.47)

(65) Prior Publication Data

US 2011/0009707 A1 Jan. 13, 2011

Related U.S. Application Data

(60) Provisional application No. 61/051,221, filed on May 7, 2008.

(51) Int. Cl.
*G06Q 10/00* (2012.01)
*G06Q 50/00* (2012.01)

(52) U.S. Cl.
USPC .......................................................... 705/2

(58) Field of Classification Search
USPC ....................................................... 705/2, 3
See application file for complete search history.

(56) References Cited

U.S. PATENT DOCUMENTS

| | | | |
|---|---|---|---|
| 4,489,387 A | 12/1984 | Lamb et al. | |
| 4,722,349 A | 2/1988 | Baumberg | |
| 4,858,121 A | 8/1989 | Barber et al. | |
| 5,065,315 A | 11/1991 | Garcia | |
| 5,434,611 A | 7/1995 | Tamura | |
| 5,471,382 A | 11/1995 | Tallman et al. | |
| 5,553,609 A | 9/1996 | Chen et al. | |
| 5,772,585 A | 6/1998 | Lavin et al. | |
| 5,823,948 A | 10/1998 | Ross, Jr. et al. | |
| 5,930,759 A | 7/1999 | Moore et al. | |
| 5,974,389 A | 10/1999 | Clark et al. | |
| 6,018,713 A | 1/2000 | Coli et al. | |
| 6,022,315 A | 2/2000 | Iliff | |
| 6,026,363 A | 2/2000 | Shepard | |
| 6,260,021 B1 | 7/2001 | Wong et al. | |

(Continued)

OTHER PUBLICATIONS

Gray, James E. et al. "Baby CareLink: Using the Internet and Telemedicine to Improve Care for High-Risk Infants." Pediatrics, 106(6): 1318-1325 (Dec. 2000). Retrieved from the Internet on Aug. 12, 2011, at URL: <http://pediatrics.aappublications.org/cgi/content/full/106/6/1318>.

(Continued)

*Primary Examiner* — John Pauls
*Assistant Examiner* — Trang Nguyen
(74) *Attorney, Agent, or Firm* — Bridget M. Hayden; Dorsey & Whitney LLP

(57) ABSTRACT

A telehealth communications network accessible anywhere sufficient bandwidth connection is available facilitates a medical encounter between a patient at a patient site and a provider at a provider site remotely located from the patient, and includes an operating console comprising at least one memory and at least one processor coupled to the network, the operating console configured to execute at least one workflow for facilitating the medical encounter.

14 Claims, 47 Drawing Sheets

(56) References Cited

U.S. PATENT DOCUMENTS

| | | | |
|---|---|---|---|
| 6,263,330 B1 | 7/2001 | Bessette | |
| 6,272,481 B1 | 8/2001 | Lawrence et al. | |
| 6,347,329 B1 | 2/2002 | Evans | |
| 6,645,142 B2 | 11/2003 | Braig et al. | |
| 6,656,115 B1 | 12/2003 | Miyazaki et al. | |
| 6,735,551 B2 | 5/2004 | Voegeli et al. | |
| 6,742,895 B2* | 6/2004 | Robin | 351/246 |
| 6,804,656 B1 | 10/2004 | Rosenfeld et al. | |
| 6,820,057 B1 | 11/2004 | Loch et al. | |
| 6,915,266 B1 | 7/2005 | Saeed et al. | |
| 6,958,706 B2 | 10/2005 | Chaco et al. | |
| 6,962,715 B2 | 11/2005 | Lee et al. | |
| 7,051,120 B2 | 5/2006 | Greene et al. | |
| 7,076,437 B1 | 7/2006 | Levy | |
| 7,080,098 B2 | 7/2006 | Smirniotopoulos et al. | |
| 7,103,666 B2 | 9/2006 | Royer et al. | |
| 7,120,636 B2 | 10/2006 | Pendleton | |
| 7,156,809 B2 | 1/2007 | Quy | |
| 7,181,017 B1 | 2/2007 | Nagel et al. | |
| 7,234,064 B2* | 6/2007 | Menschik et al. | 713/193 |
| 7,251,610 B2 | 7/2007 | Alban et al. | |
| 7,256,708 B2 | 8/2007 | Rosenfeld et al. | |
| 7,286,997 B2 | 10/2007 | Spector et al. | |
| 7,295,988 B1 | 11/2007 | Reeves | |
| 7,298,836 B2 | 11/2007 | Wellons et al. | |
| 7,305,359 B2 | 12/2007 | Bonnell | |
| 7,307,543 B2 | 12/2007 | Rosenfeld et al. | |
| 7,313,529 B2 | 12/2007 | Thompson | |
| 7,315,535 B2 | 1/2008 | Schuman | |
| 7,315,825 B2 | 1/2008 | Rosenfeld et al. | |
| 7,318,059 B2 | 1/2008 | Thomas et al. | |
| 7,321,862 B2 | 1/2008 | Rosenfeld et al. | |
| 7,325,076 B1 | 1/2008 | Morrison et al. | |
| 7,395,216 B2 | 7/2008 | Rosenfeld et al. | |
| 7,411,509 B2 | 8/2008 | Rosenfeld et al. | |
| 7,433,827 B2 | 10/2008 | Rosenfeld et al. | |
| 7,454,359 B2 | 11/2008 | Rosenfeld et al. | |
| 7,454,360 B2 | 11/2008 | Rosenfeld et al. | |
| 7,467,094 B2 | 12/2008 | Rosenfeld et al. | |
| 7,475,019 B2 | 1/2009 | Rosenfeld et al. | |
| 7,650,291 B2 | 1/2010 | Rosenfeld et al. | |
| 7,912,733 B2* | 3/2011 | Clements et al. | 705/2 |
| 7,956,894 B2* | 6/2011 | Akers et al. | 348/207.1 |
| 7,991,625 B2 | 8/2011 | Rosenfeld et al. | |
| 8,170,887 B2 | 5/2012 | Rosenfeld et al. | |
| 8,175,895 B2 | 5/2012 | Rosenfeld et al. | |
| 2001/0032100 A1 | 10/2001 | Mahmud et al. | |
| 2001/0039504 A1 | 11/2001 | Linberg et al. | |
| 2001/0041991 A1 | 11/2001 | Segal et al. | |
| 2002/0143276 A1 | 10/2002 | Ernst | |
| 2003/0195787 A1 | 10/2003 | Brunk et al. | |
| 2004/0019501 A1 | 1/2004 | White et al. | |
| 2004/0116785 A1* | 6/2004 | Bulat | 600/300 |
| 2004/0125938 A1 | 7/2004 | Turcan et al. | |
| 2004/0158486 A1 | 8/2004 | Nudd et al. | |
| 2004/0210458 A1 | 10/2004 | Evans et al. | |
| 2004/0220829 A1 | 11/2004 | Baharav et al. | |
| 2005/0027995 A1* | 2/2005 | Menschik et al. | 713/193 |
| 2005/0149364 A1* | 7/2005 | Ombrellaro | 705/3 |
| 2006/0041450 A1* | 2/2006 | Dugan | 705/2 |
| 2006/0064319 A1 | 3/2006 | Loevner | |
| 2006/0116911 A1 | 6/2006 | Tremblay et al. | |
| 2006/0276714 A1 | 12/2006 | Holt et al. | |
| 2006/0277075 A1 | 12/2006 | Salwan | |
| 2007/0041626 A1 | 2/2007 | Weiss et al. | |
| 2007/0130287 A1* | 6/2007 | Kumar et al. | 709/217 |
| 2007/0136095 A1* | 6/2007 | Weinstein | 705/2 |
| 2007/0179361 A1 | 8/2007 | Brown et al. | |
| 2007/0203753 A1 | 8/2007 | Hasan et al. | |
| 2007/0219823 A1 | 9/2007 | Warner | |
| 2007/0263563 A1 | 11/2007 | Biagioni et al. | |
| 2007/0271117 A1 | 11/2007 | Klein et al. | |
| 2007/0276702 A1 | 11/2007 | Dani | |
| 2008/0004904 A1 | 1/2008 | Tran | |
| 2008/0015894 A1 | 1/2008 | Miller et al. | |
| 2008/0045811 A1 | 2/2008 | Iliff | |
| 2008/0046286 A1 | 2/2008 | Halsted | |
| 2008/0046295 A1 | 2/2008 | Albrecht | |
| 2008/0126133 A1* | 5/2008 | Park | 705/3 |
| 2009/0216564 A1 | 8/2009 | Rosenfeld et al. | |

OTHER PUBLICATIONS

"ICTs and Sustainable Development," The Communication Initiative Network, published Jun. 2, 2007. Retrieved from the Internet on Sep. 9, 2011, at URL: <http://www.comminit.com/?q=global/node/223870>.

"Building a Statewide Program (M1A)," American Telemedicine Association, Concurrent Sessions, 2007. Retrieved from the Internet on Sep. 9, 2011, at URL: <http://www.atmeda.org/conf/2007/concurrent.htm>.

* cited by examiner

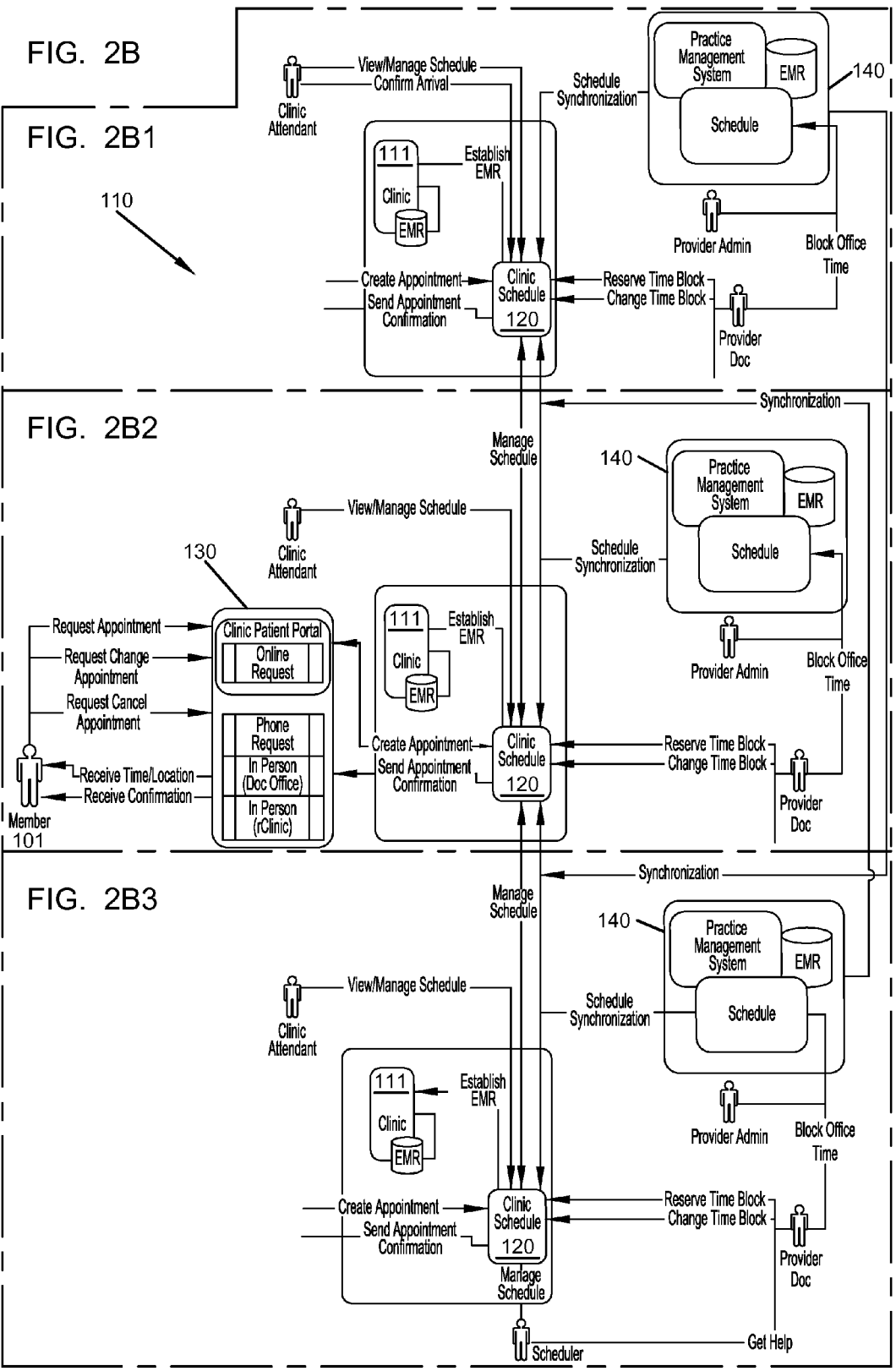

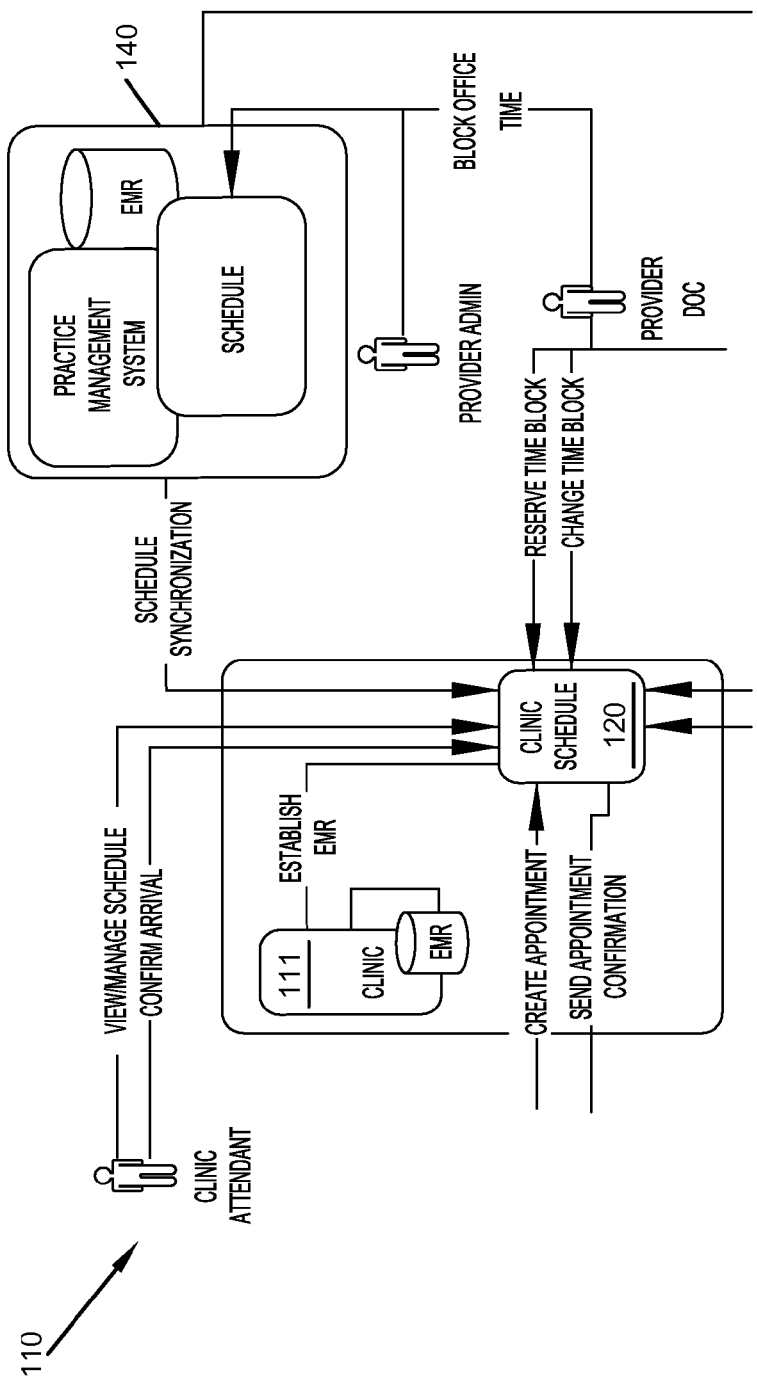
FIG. 2B1

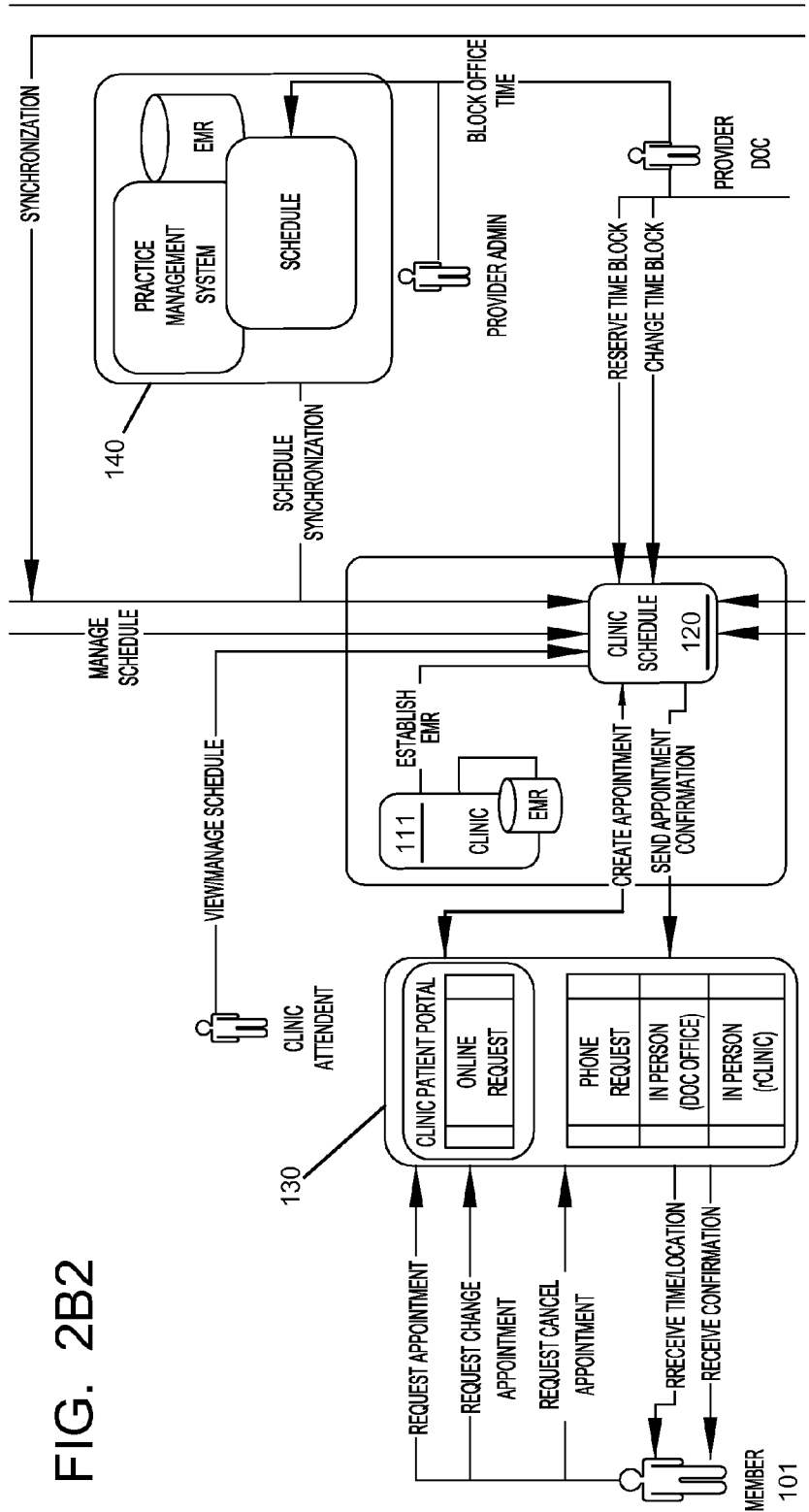
FIG. 2B2

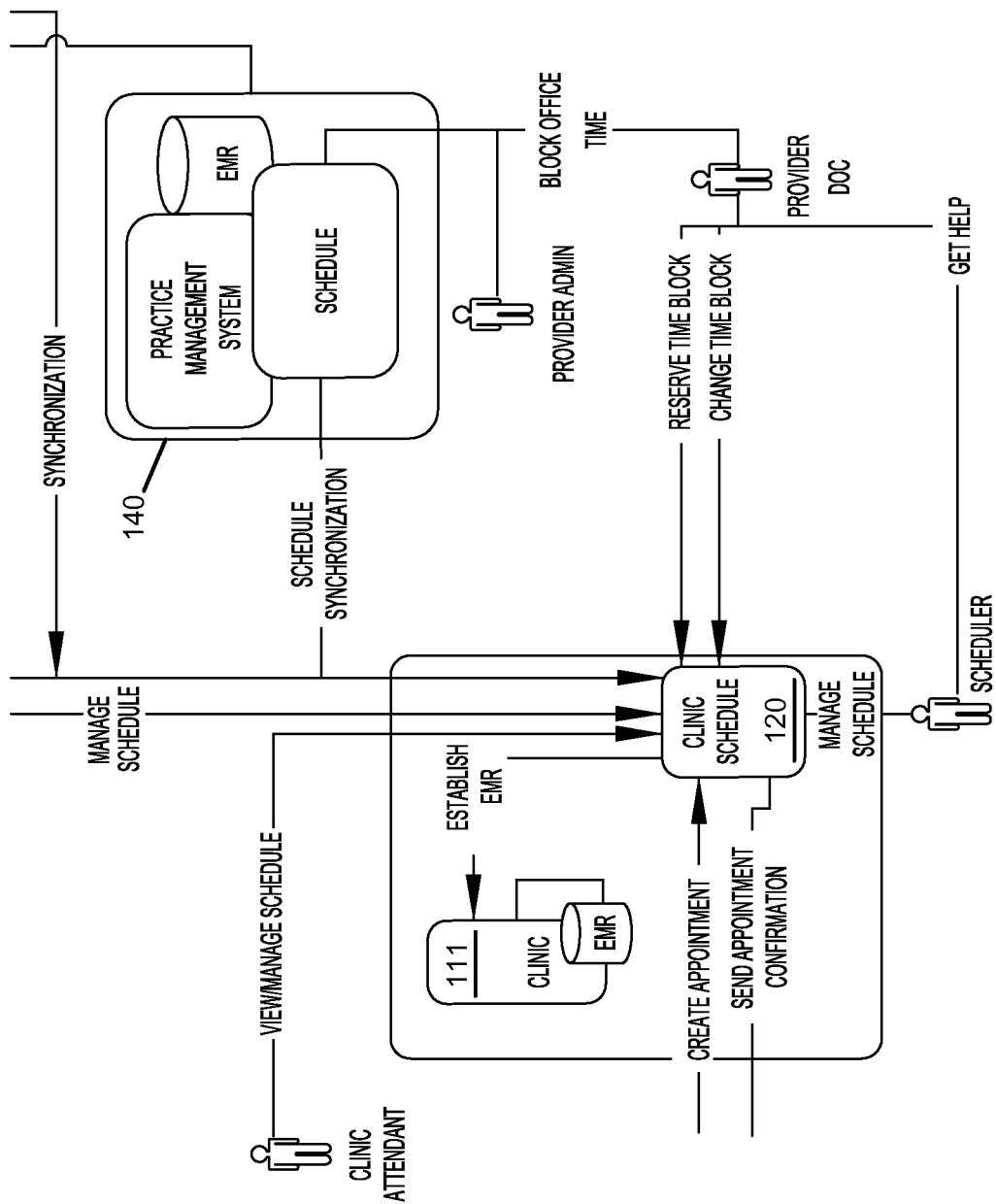
FIG. 2B3

FIG. 14

Onsite Telemedicine Clinic Log In

Branding Image

Rainier VirtualClinic Center
ATTWSWASEA001
Monday, March 23, 2009  8:59 AM

If you need assistance
800-555-5555

Missing required information.
Please fill out the required information and try again.

Log in to get started.

User Name: NoSuchUser    Required
Password: **********    Required

[ Exit ]    [ Log In ]

---

Onsite Telemedicine Clinic Log In

Branding Image

Rainier VirtualClinic Center
ATTWSWASEA001
Monday, March 23, 2009  8:59 AM

If you need assistance
800-555-5555

User Name or Password error.
The User Name and Password you have entered is incorrect. Please check your information and try again.
After three failed log in attempts, we will lock you account for security purposes

Log in to get started.

User Name: NoSuchUser
Password: **********

[ Exit ]    [ Log In ]

---

Onsite Telemedicine Clinic Log In

Branding Image

Rainier VirtualClinic Center
ATTWSWASEA001
Monday, March 23, 2009  8:59 AM

If you need assistance
800-555-5555

Too many failed Log In attempts.
For security reasons, your account has been locked. To unlock your account, you must contact support to confirm you log in information and to unlock your account. Please call 800-555-5555

Log in to get started.

User Name: NoSuchUser
Password: **********

[ Exit ]    [ Log In ]

FIG. 20

Schedule: 03/23/2009 for Rainier VirtualClinic Center    Printed: 03/23/2009; 7:59AM 8:30 AM; Thompson, Christopher; Cardiovascular irregularities; Workflow not complete
9:15 AM; Thompson, Christopher; Cardiovascular irregularities; Patient Checked In
! 9:45 AM; Appt No-Go; Brown, Joeseph: Rash; This site's req. device unavailable;
10:00 AM; Madeup, Laszlo; Knee pain;
10:45 AM; Lastname, Firstname; Appointment Reason; Workflow State and Notes.
11:30 AM; Lastname, Firstname; Appointment Reason; Workflow State and Notes.
11:45 AM; Lastname, Firstname; Appointment Reason; Workflow State and Notes.
1:00 PM—1:30 PM; Lastname, Firstname; Appointment Reason; Workflow State and Notes Note: The "Overview" (above) and each appointment should print on their own page.

8:30 AM Lastname, Firstname; Appointment Reason; Workflow State.

Appointment Information

| | |
|---|---|
| Begins: | mm/dd/yyyy at hh:mm AM |
| Ends: | mm/dd/yyyy at hh:mm AM |
| Status: | Patient Check-In IN PROGRESS (at kiosk) |
| Reason: | Appointment Reason |
| Notes: | Appointment Reason Notes area; User Entered text that might further describe the selected "Appointment Reason". |
| Type: | Visit Type |
| Intake Forms: | General Questionnaire: last updated Feb 14, 2009 |
| | Social History: last updated Feb 14, 2009 |
| | Surgical and Allergies: last updated Jan 1, 2009 |
| | Immunization Form: last updated Feb 14, 2009 |
| PHR: | Google Health: view shared PHR Information |
| | Previous Visit Info: view last 5 visits |

Sites

Clinic Site: Rainier VirtualClinic Center
ATTWSWASEA001

Dr. Site: Doctor Park eHealth Plaza
DOCWSMNMPLS005

Patient

| | |
|---|---|
| Name: | Lastame, Firstname; M.; Mr. |
| Date of Birth: | 01/01/1970 |

Contact

| | |
|---|---|
| Address: | 1234 Prepopulated St NE |
| Line 2 (apt/suite): | Apartment 241 |
| City, State Zip: | Minneapolis, MN 55443 |
| Preferred Phone: | 555-555-5555 |
| Preferred Email: | JoeUser@whereiwork.com |

Insurance

| | |
|---|---|
| Employer: | CISCO |
| Primary Insurance: | Cigna Health Care |
| Group Number: | 1234567 |
| Subscriber ID: | 12345678901 |
| Relationship*: | Subscriber (self) |

TELEHEALTH SCHEDULING AND COMMUNICATIONS NETWORK

CROSS-REFERENCE TO RELATED APPLICATIONS

This application claims the benefit of U.S. provisional patent application Ser. No. 61/051,221, filed May 7, 2008, the content of which is hereby incorporated by reference in its entirety.

FIELD OF THE INVENTION

The present invention provides a telehealth scheduling and communications network.

BACKGROUND

The current medical diagnostic and treatment environment is populated with traditional medical clinics and establishments consisting of physicians and other medical staff located in central office settings. The customer visits the provider at the central office location for examinations, follow-up appointments, diagnostic tests, and treatment. If other provider opinions or treatments are required, the customer must schedule those appointments separately and subsequently visit those providers at a later date at other locations. Often, specialists or other providers are located in other cities. This can be a hardship, particularly for those customers located in rural areas or in countries having sparse medical coverage. Some relief may be available for homebound customers able to receive home healthcare visits from a nurse or physician, but this creates a hardship for the medical professional that is unable to provide a volume of care to their patients due to travel time constraints, and only certain medical professionals may be available to make home visits. In addition, the more remote the patient's home is located, the less likely it is that any medical professional will provide home healthcare. Some patients may visit a clinic equipped with video conferencing capabilities and may interface with a remotely located physician having an association with the clinic in order to receive care. This arrangement is a small scale operation, and the patient needs access to the specific clinic having conferencing capabilities in order to interface with their physician. Although healthcare access may be provided in this manner, the patient is limited to receiving care from the physician(s) associated with the clinic. Geographic constraints may thus hinder access, quality and variety of healthcare for patients.

In situations where a patient is located away from their preferred doctor and possibly away from their insurance network, e.g., while traveling, locating and receiving affordable healthcare may be difficult. If a patient is seen by a doctor outside of the patient's insurance network, for example, the patient may be responsible for all or at least a larger portion of the medical expenses incurred. As a result, patients may be constrained by their health insurance network as to where healthcare may be received.

Moreover, as medical specialties continue to evolve, the diagnosis and treatment methodology will involve many more providers and specialists than currently accessed. For those customers who have ongoing or complex medical conditions requiring coordinated care, the scheduling and care coordination process for multiple providers is burdensome. Also, providers are not aware of the entire treatment prescribed by other providers. This lack of communication reduces quality of care for the customer.

Accordingly, there is a need to provide a healthcare network that allows patients to receive healthcare anywhere that is accessible by a communications network so that the patient may receive high quality care regardless of their geographical location or the location of their health insurance company.

SUMMARY OF THE INVENTION

The present disclosure provides a telehealth communications network that provides ubiquitous access to healthcare and creates a continuum from monitoring a patient to dispensing care, in addition to supporting a proactively scheduled, appointment. The telehealth communications network includes hardware and software systems that allow simultaneous communication between one or more providers, e.g., physicians, and customers, e.g., patients, and/or care givers. Real-time decision making for treatments is possible via the network and the business processes provided therein. In certain implementations, the telehealth communications network may be controlled by a health insurance provider and may provide all insureds access to the telehealth communications network so that the insured may receive healthcare anywhere sufficient bandwidth connection is available.

Certain embodiments provide a telehealth communications network configured for facilitating a medical encounter between a patient at a patient site and a provider at a provider site remotely located from the patient, and includes an operating console having at least one memory and at least one processor coupled to the network, the operating console configured to execute at least one workflow for facilitating the medical encounter.

In some embodiments, a workflow is provided for implementing across a multi-site medical network accessible anywhere sufficient bandwidth connection is available, the administrative and clinical business processes involved in delivering benefits to physicians and patients, the workflow involving providing a user access to the network based on the role of the user, wherein the role of the user is one of a patient, physician, attendant and administrator; controlling the transmission and receipt of data across the multi-site medical network in response to workflow processes engaged in by the user; and guiding the user through at least one of a clinical or business process for facilitating communications with other network users located remotely from the user.

The features and advantages of the present invention will become apparent to those skilled in the art from the following detailed description, wherein it is shown and described illustrative implementations of the invention, including best modes contemplated for carrying out the invention. As it will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 2A, 2B1, 2B2 and 2B3 are block diagrams of the operation of the scheduling components of the telehealth communications network.

FIGS. 10-39 provide a series of workflows and functions that may be encountered by users.

DETAILED DESCRIPTION

Overview

A telehealth communications network includes communicatively coupled hardware and software systems that enables both real-time communication and appointment scheduling between one or more providers (e.g., physicians), customers (e.g., patients) and/or care givers. In use, the telehealth communications network is a dynamic network that enables parties to engage in a communication session on-demand for the real-time diagnosis and treatment of customers by qualified, remotely located providers. Communication sessions may be facilitated electronically by providing some or all participants with a customer's medical records via the telehealth communications network. In some implementations, a provider may have the ability to electronically prescribe medications for the customer using the telehealth communications network.

Figure 1A:
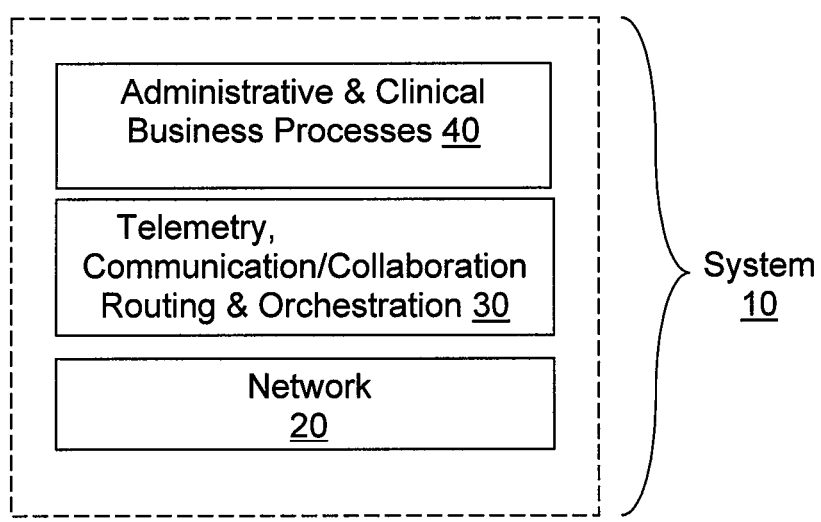
FIG. 1A depicts a conceptual system architecture for implementing a communication system that enables dynamic interactions between providers and customers in order to provide a telehealth communications network.

FIG. 1A depicts a conceptual system architecture for implementing a telehealth communications network that enables dynamic interactions between providers and customers. The conceptual system 10 is composed of layers having various functions and interdependencies and includes: network layer 20, telemetry, communication/collaboration routing and orchestration layer 30 and administrative and clinical business layer 40. Network layer 20 implements computer hosting and network management capabilities and may be supported by a network carrier, for example. Telemetry, communication/collaboration routing and orchestration capabilities layer 30 may include network intelligence for routing and orchestration of business and technical events across the network layer 20. This layer may be supported by an internetworking company, such as Cisco Telepresence. Administrative and clinical business layer 40 provides various workflows pertaining to the administrative and clinical business processes involved in delivering benefits to providers and customers, and may be supported by a health insurance company.

According to certain embodiments, the telehealth communications network is implemented across a multi-site medical network configured with a communications platform for transmitting and receiving data, audio and visual images at multiple locations perceptually simultaneously (e.g., in real-time) using high-speed networks and video conferencing capabilities (e.g., audio and visual interfaces and monitors) at each location site. The multi-site medical network is a macro solution to healthcare access and may be provided on a city, state or country-wide basis, and may be accessible anywhere a sufficient bandwidth connection is available. Where an insurance company supports the telehealth communications network, a patient/insured may thus be provided with access to covered healthcare virtually anywhere, and the patient's geographic location relative to the insurance company's network area does not constrain access to healthcare.

For example, a patient located in a state or country outside of their insurance network area, e.g., outside of the patient's state of residence, having a medical need may be seen by a physician located remotely and within their insurance network by engaging in a physician-patient encounter through accessing the telehealth communications network supported by their insurance company by way of a sufficient bandwidth connection, e.g., from a point-of-care site, which may be a mobile phone, a kiosk or clinic. The patient may provide the required permissions to the telehealth communications network to authorize the encounter and allow access to health records. The physician, which may be the patient's primary physician, may have an electronic medical record (EMR) on hand, or the EMR may be made available through the telehealth communications network through a series of permissions obtained by the patient and/or physician, and the physician may thus be apprised of the patient's past medical history before and during the encounter, regardless of the patient's location. Subsequently, the physician may update the EMR, and possibly a patient health record (PHR), following the visit. In addition, the telehealth communications network may update a patient's PHR based on the patient's request and assignment of permission to the system. Appointment details such as bandwidth usage and procedures conducted may be recorded and tracked for insurance payment and reimbursement purposes. As a result, the telehealth communications network provides patients and physicians access to each other and to medical records, and details of the encounter may be recorded for insurance purposes.

Figure 1B:
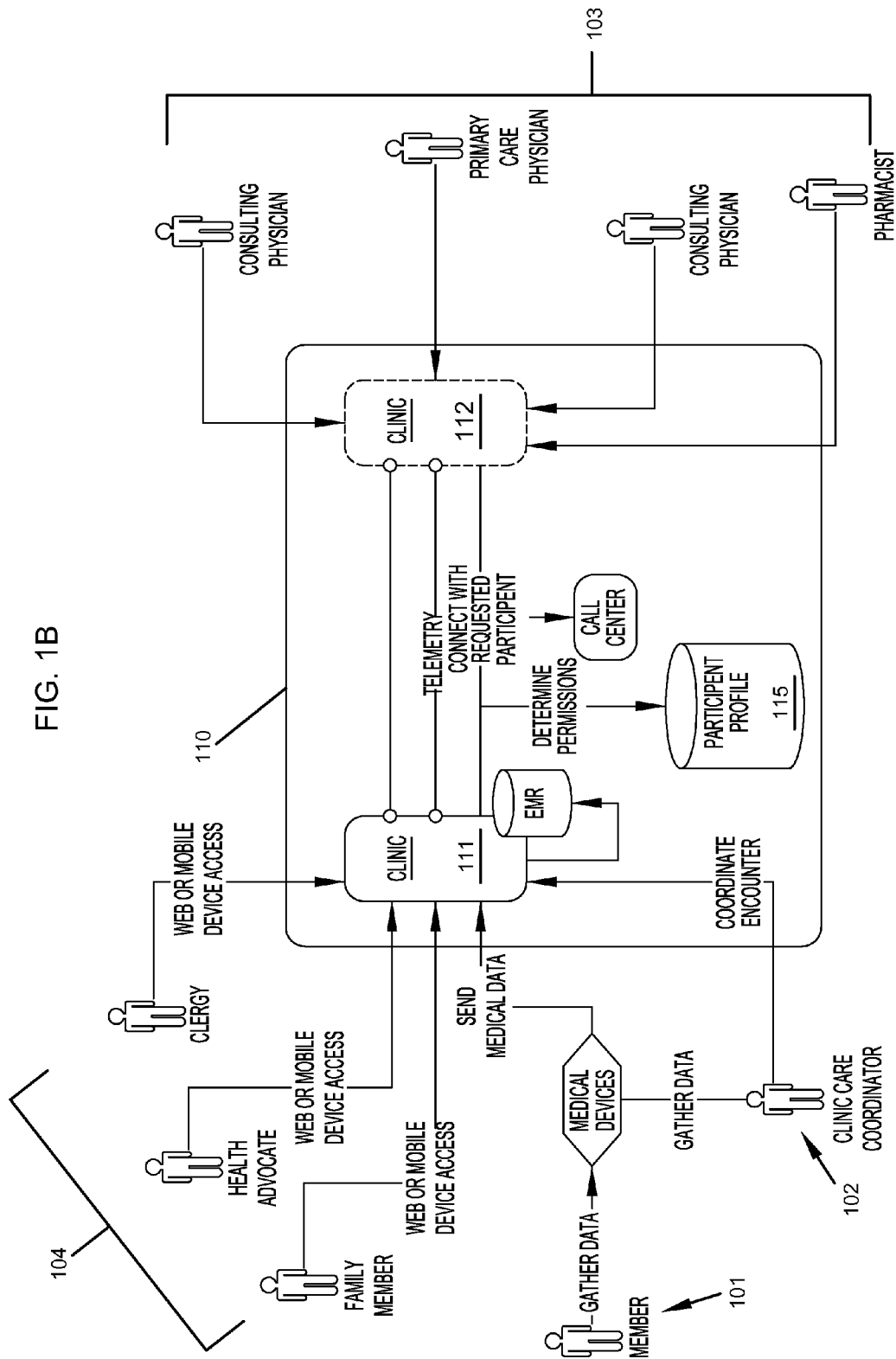
FIG. 1B is a block diagram of a the telehealth communications network configured as a common integrated network that facilitates provider-customer interaction on a many-to-many basis.

FIG. 1B is a block diagram of a the telehealth communications network 110 configured as a common integrated network that facilitates provider-customer appointment scheduling via a scheduling platform, and that facilitates interaction on a many-to-many basis via a communications platform. According to FIG. 1B, customers 101, e.g., members, and clinic care coordinators 102 located at clinics 111 engage in a scheduled communication session with a number of providers 103 located at provider facilities 112, which are remote from clinics 111 and the member 101. In addition, third parties 104, including family members, health advocates and clergy, may be located at clinics 111 and may participate in the communication session. In some implementations, when multiple parties are involved in the appointment, each party may be able to see and hear all other parties at the same time. However, according to certain implementations, a customer 101 may have discretion as to whether or not to share each participants' view of visual screens by setting profile settings stored in participant profile database 115.

Thus, a customer 101 may have the ability to customize a provider and/or third party experience with the customer based on the customer's preference. Although FIG. 1B is described in the context of a clinic 111, any point-of-care site may be provided according to the embodiments provided herein, which may or may not involve a care coordinator 102 being present at the point-of-care site.

Scheduling Platform

Figure 2A:
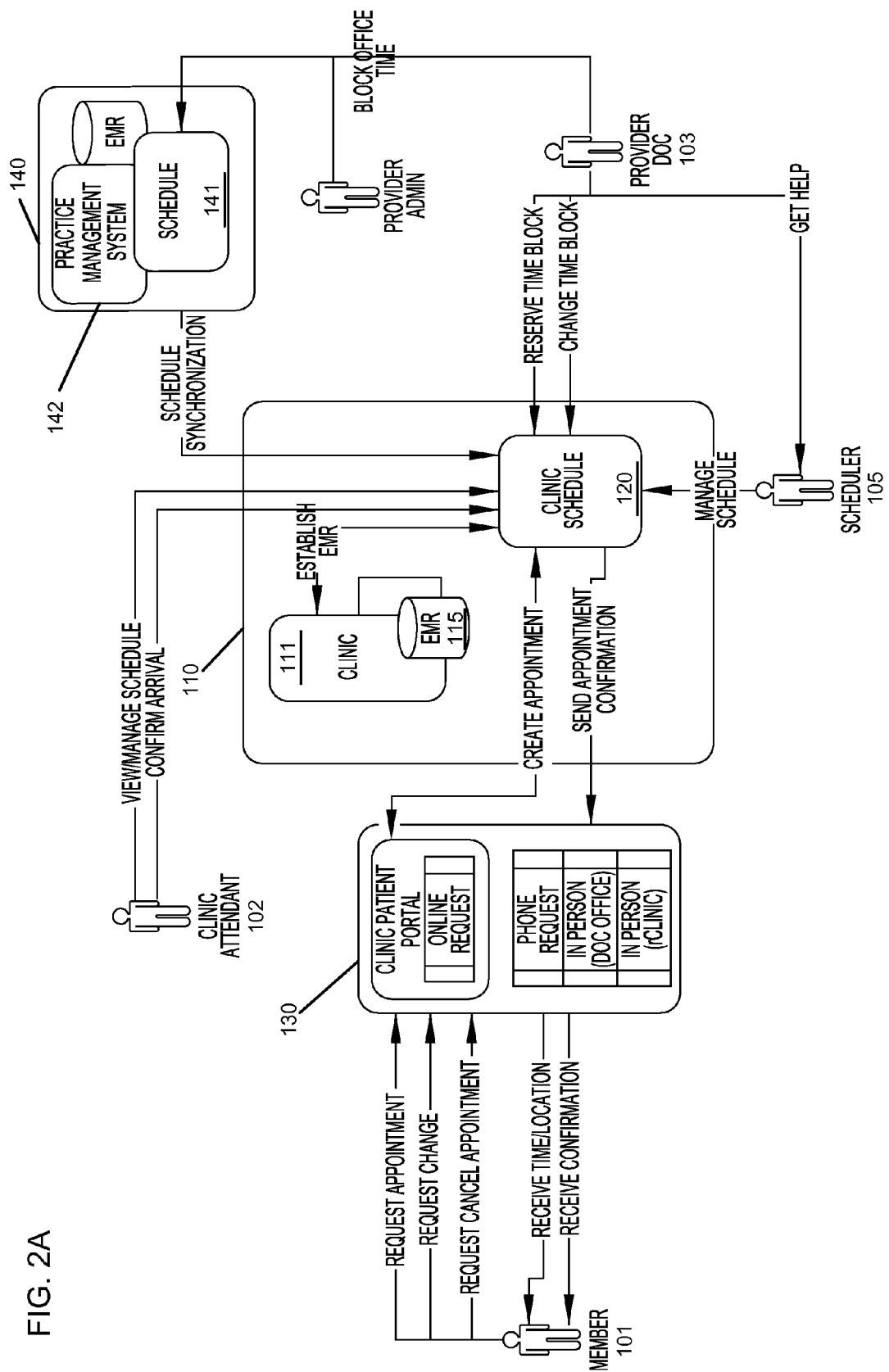

In certain embodiments of the present invention, the telehealth communications network 110 includes business processes for facilitating appointment scheduling among remotely located parties. FIG. 2A is a block diagram depicting the operation of scheduling components 120, 130, 140 forming a centralized scheduling system on the telehealth communications network 110. A centralized network appointment scheduling tool 120 is for maintaining and updating clinic and provider schedules, and a customer portal 130 and a provider portal 140 are for accessing the scheduling tool 120.

Scheduling tool 120 in the centralized scheduling system stores and transmits customer-provider schedule data and clinic and provider availability data. Appointment schedules for a number of providers clinics may be stored via scheduling tool 120, and customers may schedule appointments with a provider based on a clinic's and/or a provider's availability. In some implementations, a scheduler 105 interacts with the scheduling tool in order to enter a provider's availability for scheduling and/or to schedule an appointment between various parties.

According to some implementations, scheduling tool 120 may be accessed by a customer via customer portal 130 where a customer may schedule appointments at a clinic with one or more providers, care givers and/or other third parties remotely located from the clinic. For example, a customer may initiate appointment scheduling using a telephone or an online web interface coupled to customer portal 130.

Where a toll-free or local telephone number provides a customer access to the customer portal 130, the customer may engage in an interactive voice response scheduling system integrated to a centralized scheduling system or clinic messaging system. The interactive system may include prompts for scheduling an appointment at a particular clinic, or may convey open appointments for proximately located clinics and for one or more providers and/or care givers specified by the customer. Prompts related to identifying a provider or type of provider the customer would like to communicate with may also be provided. For example, a customer may select the type of provider (e.g., specialty, cost, gender, practice location by city, state, region, country, proximity to clinic, affiliation, spoken language, and/or physician/hospital quality ranking) they want to schedule an appointment with using a voice or touch activated prompt. In addition, customer portal 130 may also provide a customer with prompts for validating customer information and insurance information. Upon scheduling an appointment, appointment information may be accessed via the telehealth communications network 110.

In addition or alternatively, the customer portal 130 may be a web-based system communicatively coupled to the scheduling tool 120. Accordingly, a customer may access the customer portal 130 via the Internet, and the web-based system may include customer log-in, identification and validation screens for entering customer specific information. In addition, the scheduling system may include screens for entering insurance information. A customer may search for providers by type using various search criteria (e.g., specialty, cost, gender, practice location by city, state, region, country, proximity to clinic, affiliation, spoken language, and/or physician/hospital quality ranking) or may identify a particular provider for scheduling an appointment, and the customer may be presented with scheduling tools showing open appointments for one or more providers and/or care givers that match the customer's specifications. According to further embodiments, a customer accessing customer portal 130 may request appointments for specific days or times at a particular clinic or with a particular provider. The centralized scheduling system may send the customer a response indicating which clinic is available that matches the availability of the selected remotely located provider(s). Alternatively, the centralized scheduling system may send the customer a response indicating which remotely located provider is available at the same time a particular clinic is available.

In certain implementations, customer portal 130 may not need to be available in order to schedule an appointment. Instead, a scheduler 105 serves as an appointment facilitator and enters appointment and customer information into the centralized scheduling system, e.g., directly into scheduling tool 120. In response, scheduler 105 may receive instructions or data from the centralized scheduling system and relay pertinent scheduling information to a customer. For example, after a customer visits clinic 111 and finishes their scheduled appointment, new appointment instructions may be given to the customer 101 in paper form prior to leaving the clinic 111. In addition, the appointment instructions may be electronically recorded and be made available for all parties associated with the appointment.

The scheduling tool 120 is also associated with a provider portal 140 that allows providers to enter their availability for appointments. For example, provider portal 140 may include an electronic schedule 141 and a practice management system 142. The electronic schedule 141 may be synchronized with the clinic schedule via the scheduling tool 120 periodically or on a continuous basis. In addition, in some implementations, providers 103 and/or schedulers 105 may manage a provider's clinic schedule by directly accessing the scheduling tool 120. For example, where a provider 103 has a last minute change in their schedule, the provider may access the scheduling tool 120 directly via the Internet or may contact a scheduler 105 in order to make schedule changes. Accordingly, the centralized scheduling system allows multiple providers and care givers to enter their availability for scheduled appointments. In addition, practice management system 142 may store provider profiles that includes data related to the provider including information regarding a provider's practice, specialty, clinic/business location, proximity to customer clinics, proximity to hospitals near customer clinics, cost, gender, affiliation, spoken language, and/or physician/hospital quality ranking. The provider profile information may be accessed or retrieved by the centralized scheduling system in order to match customers with providers based on a customer's requests or data within a customer's electronic medical record.

In some implementations, scheduling software associated with a provider portal 140 may be installed on a provider's computer and/or a provider may access the provider portal 140 via the telehealth communications network. The provider or third party schedule may be uploaded into the scheduling tool 120, which facilitates providing a centralized scheduling system. Software installed on a provider's system may integrate with the central scheduling tool 120 located on virtual clinic network servers. In some configurations, the link between the central scheduling tool 120 and the provider portal 140 may be implemented using standard health information software that conforms to the HL7 standard. Each provider or third party schedule may then be made available to the customer for scheduling appointments.

FIG. 2B1 is a block diagram depicting the operation of another centralized scheduling system on the telehealth communications network 110. FIG. 2B2 includes customer portal 130, and multiple sets of scheduling tools 120 and provider portals 140. Scheduling tools 120 may communicate with each other, and each of the provider portals may communicate with the scheduling tools 120 in order to synchronize provider schedules across clinics. Once a provider is scheduled to communicate with a customer at one clinic, each of the other clinic schedules are updated to make the provider unavailable during the scheduled appointment. It should be understood that the centralized scheduling system is not limited to providing a scheduling tool 120 for each clinic or a single provider portal for each provider or provider group. Instead, the centralized scheduling system may include a single scheduling tool 120 for all clinics, a single provider portal 140 for all providers, a number of scheduling tools 120 different from the number of clinics, and/or a number of provider portals 140 different from the number of providers or provider groups.

Implementing a centralized scheduling system according to FIG. 2B3 may provide advantages to customers having access to multiple clinics. According to FIG. 2B3, customers accessing customer portal 130 that have access to multiple clinics 111, and that are interested in scheduling an appointment at a particular time, may enter their appointment date and time preferences and receive clinic availability output from customer portal 130, along with provider availability for the specified time. For example, two of three clinics accessible to the customer may be available for the customer to visit at a time and date selected by the customer, and any number of remotely located providers may be available to communicate with the customer via the telehealth communications network. In this case, the customer may select which clinic they will visit and which provider they will communicate with. In another example, a customer accessing customer portal 130 may enter their preference for scheduling an appointment with a particular provider, and the customer may receive output on which clinics have openings for the customer to communicate with the remotely located provider of their choosing. In each example, customer portal 130 queries the scheduling tools 120 for the clinics 111 and determines availability based on the customer's preferences and a provider's profile.

In each of the above examples, scheduling tool 120 matches a customer's requirements with the appropriate provider(s) or resource(s) on a real-time basis. Furthermore, the scheduling tool 120 may access a customer's electronic medical record, receive the requirements entered by the customer, and then may match the customer with the appropriate provider or resource based on multiple variables.

Communications Platform

The telehealth communications network may be configured as a common integrated network that facilitates provider-customer interaction on a many-to-many basis. Clinics and private practice offices, domestic and international contact centers, customer service centers, payment centers allowing point of care payment, health and financial services centers, health pods, homes, phones, mobile devices and mobile healthcare vehicles may be communicatively coupled via the telehealth communications network to provide an integrated network. By enabling the various parties to be involved in a communications session, which are in addition to physicians and patients, certain embodiments provide medical services to participants in a hosted manner. Furthermore, the telehealth communications network is not limited to communications between domestic parties and instead allows any of the participants in the telehealth communications network located anywhere in the world to communicate with each other.

Figure 3A:
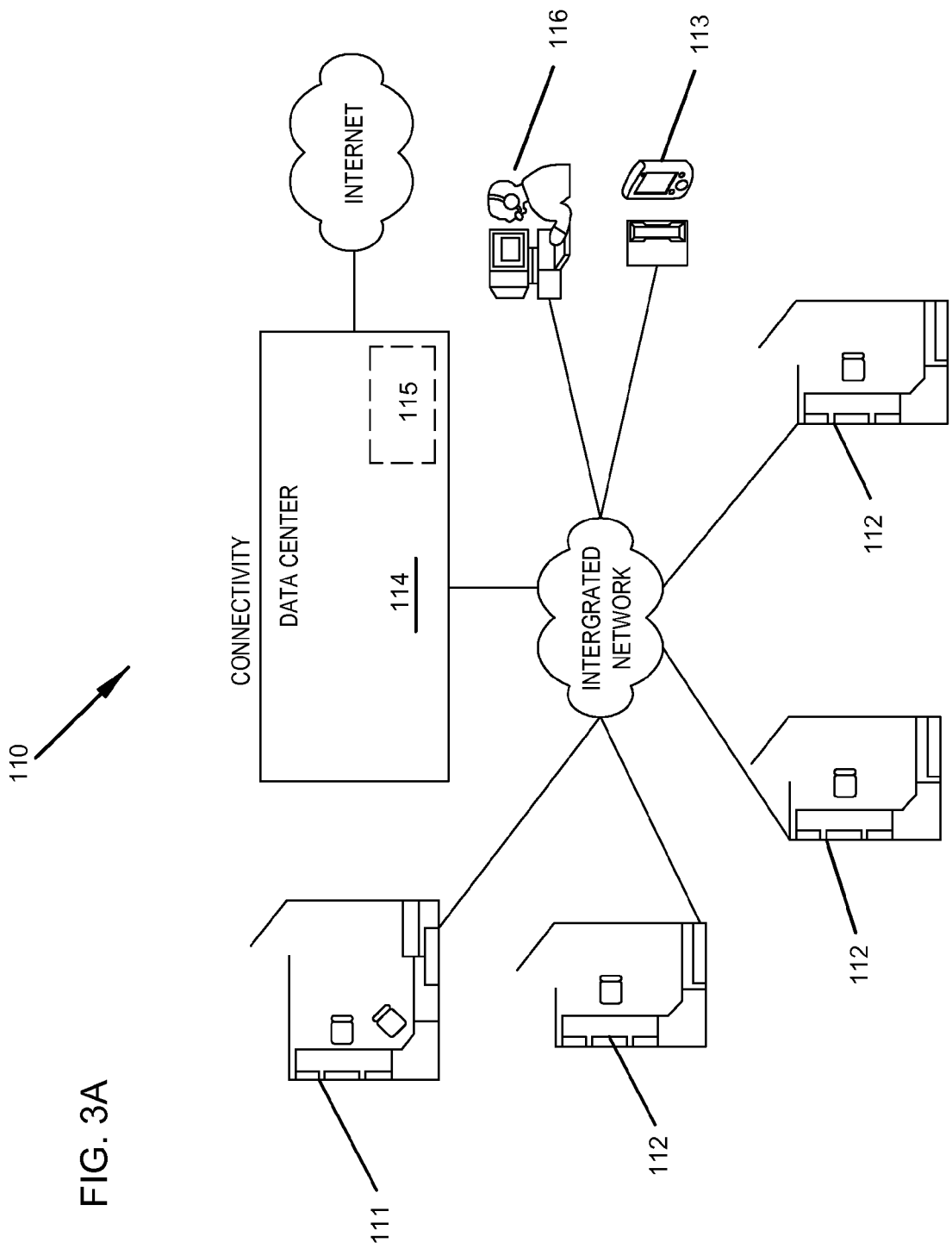
FIG. 3A illustrates the components of an integrated telehealth communications network.

FIG. 3A illustrates various locations associated with an integrated telehealth communications network 110. Providing a telehealth communications network that communicatively couples customers, providers and third parties at multiple points of access enables users to interact with each other, and allows third parties to oversee the diagnosis and treatment of a customer. According to FIG. 3A, the telehealth communications network 110 may include communications links to various locations including clinics 111, provider facilities 112, one or more caregivers/third parties locations or access points 113, and a central data center 114 with access to a centralized call/contact center 116. In certain implementations, each of the facilities coupled to the network may use multicast technology to deliver audio and visual communications over the telehealth communications network 110. In further implementations, central data center 114 may house participant profile database 115, and each participant's access to the communication session may be controlled according to a participant's profile settings.

Figure 3B:
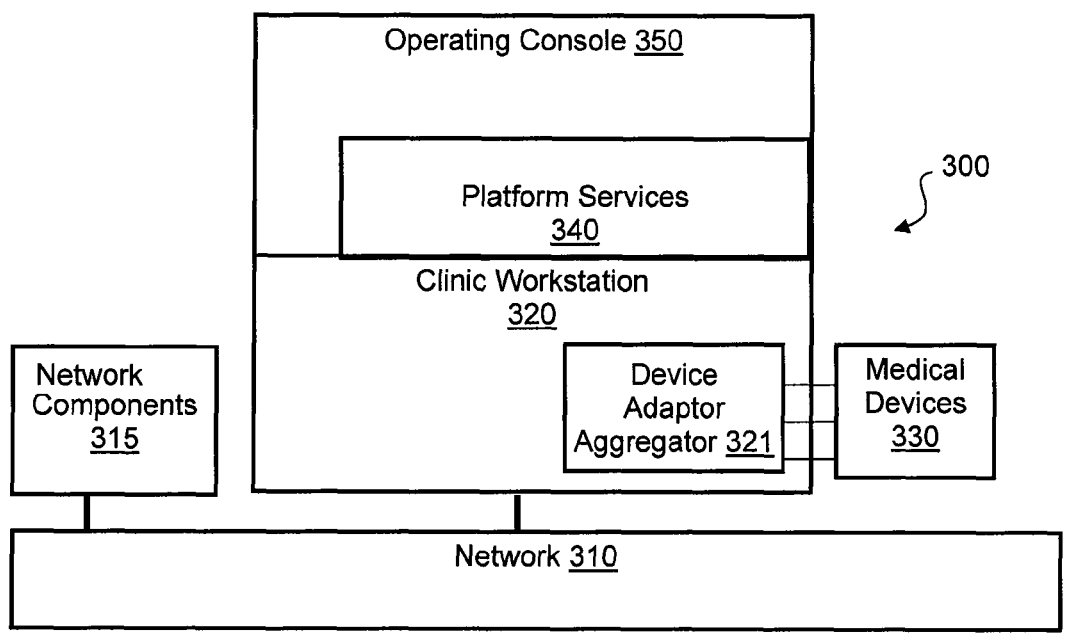
FIG. 3B illustrates a client component of the telehealth communications network.

FIG. 3B illustrates a client component 300 of the telehealth communications network 110. Client component 300 includes network 310, which supports network components 315 and clinic workstation 320 with its device adaptor/aggregator 321. In addition, client component 300 includes, medical devices 330, platform services 340 and operating console 350.

According to certain embodiments, clinic workstation supports 320 the computational needs of the clinic or kiosk (i.e., point-of-care or care-dispensing location) by hosting a device adaptor/aggregator 321, which communicatively couples to multiple medical devices and builds abstractions for the platform services 340 layer. According to further embodiments, clinic workstation 320 may be embodied by a portable device such personal mobile device including mobile phones, PDAs or portable medical device. For example, a mobile phone may be coupled to portable medical devices such as a stethoscope, a blood pressure cuff, a blood glucose monitor, etc., and medical data obtained from such devices may be sent from the mobile phone through the telehealth communications network 110 to provider facilities 112. As a result, instead of providing an integrated clinic 111 in the form of a kiosk, for example, a mobile phone including personal mobile phones or dedicated mobile phones may provide all the requirements needed in order for a patient to engage in a clinical visit with a remotely located physician. Thus, in some embodiments, medical devices may be provided with integrated adaptors for connecting to the mobile devices, and/or the mobile devised may be configured to accept medical devices, e.g., via plug-in connections. In addition or alternatively, portable medical devices may, for example, be Bluetooth™ enabled and may data send signals to the mobile device. As may be appreciated, the telehealth communications network may be accessible anywhere sufficient bandwidth connection may be established, and the location of a clinic workstation 320 is not constrained a physical structure such as a kiosk, clinic, mobile access point (e.g., health clinic van) or otherwise. Rather, the clinic workstation 320 is a control layer serving as an engine that can overlay any communications method.

The platform services layer 340 provides an interface to instrument and operate the medical devices 330 and the communication/conferencing capabilities of the network components 315.

Operating console 350 may be configured as a browser or rich Internet application (RIA) platform that supports the security needs of the network by providing authentication, authorization and accounting services and presents a workflow interface to the user, with which client, provider, and or nurse/attendant can interact. For example, upon authentication of a user, the operating console 350 will show entitlements to the user based on their role (i.e., client or patent, physician, nurse and/or clinic attendant). Entitlements may include workflows the user is authorized to perform. See e.g., FIGS. 10-39. The telehealth communications network 110 provides an immersive user experience, which simplifies the workflows provided via operating console 350.

Workflows

Workflows may be instantiated based on the user's role and the location from which they access the system. For example, the system may keep track of the clinic sites 111, e.g., kiosks and patient sites, and the provider sites 112, and based on the originating IP address, may infer whether the kiosk is a patient-side or a provider-side location. Based on the inferred role of the user, the system may dynamically change and present applicable workflows to the user. For example, a provider may login to the system, browse the day's schedule and be ready to be invited to an encounter, whereas a patient may login to the system and be led through a self check-in procedure including providing permissions as required by applicable laws (e.g., Health Insurance Portability and Accountability Act of 1996).

Figure 3C:
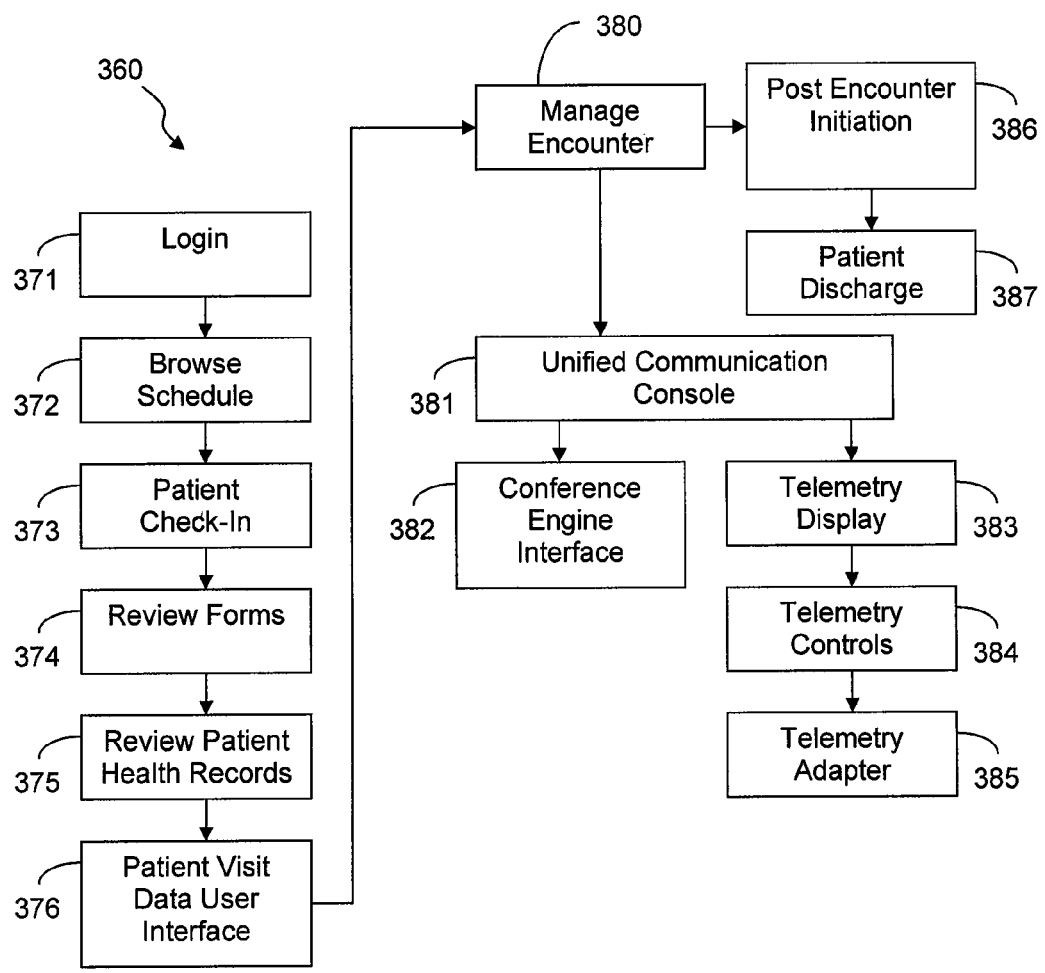
FIG. 3C illustrates a representative set of workflows and functions encountered by a nurse/attendant at a clinic that may be implemented in connection with operating console.

FIG. 3C illustrates a representative set of workflows and functions 360 encountered by a user, which may be implemented in connection with operating console 350. According to FIG. 3C, user may interface with workflows 360 by entering and viewing administrative information by performing tasks in a variety of workflows including: login workflow 371, browse schedule workflow 372, patient check-in workflow 373, review forms workflow 374 (e.g., patient consent forms, allergies, etc.), review patient health records workflow 375, and data entry in patient visit data user interface workflow 376. The patient encounter may be managed via a manage encounter workflow 380, which provides the user with access to the unified communication console 381, conference engine interface 382, telemetry display 383, telemetry controls 384, and telemetry adaptor 385, and to post-encounter initiation workflow 386 and a patient discharge workflow 387. The description of the workflows and functions 360 below primarily focuses on nurse/attendant and physician users, but secondary actors such as patients and call center representatives may utilize the functions described below.

In order to access workflows and functions 360, a computer-based system at the user site may be powered on so that boot functions initiate a starter code to detect necessary network connections and the presence of the portal application. Based on the detected components, the portal application will launch the smart client that is resident and/or download any required components or updates. During this process, the application gathers information about the software capabilities and components installed at the location (e.g., telemetry devices) and what branding/presentation layer components should be used when building the user experience for the particular location. Upon completion of this start-up cycle (see e.g., FIGS. 10-12), the network console will present a login screen to the user (see e.g., FIG. 13). In some implementations, the network is not available to the user and telemetry devices will not operate until the portal is initiated and/or is online. For example, if a user fails to enter a correct user name and password multiple times, they may be locked out of the system. See FIG. 14.

Upon initiating a portal, a standard login workflow 371 may be presented to a user of the network 110 in order to enter and execute their user identification and password. User management may be centralized as part of a set of clinic portal core services (e.g., applications/functions managed centrally for all network installations). Based on user ID and Location ID (passed with a user's credentials), the network deduces from whom and where the login originates, and this data may be used to shape the user experience including the on-screen presentation once the user is successfully logged in. For example, a patient may be presented with a self check-in process, whereas a nurse/attendant may be presented with a clinic operations experience.

Figure 17:
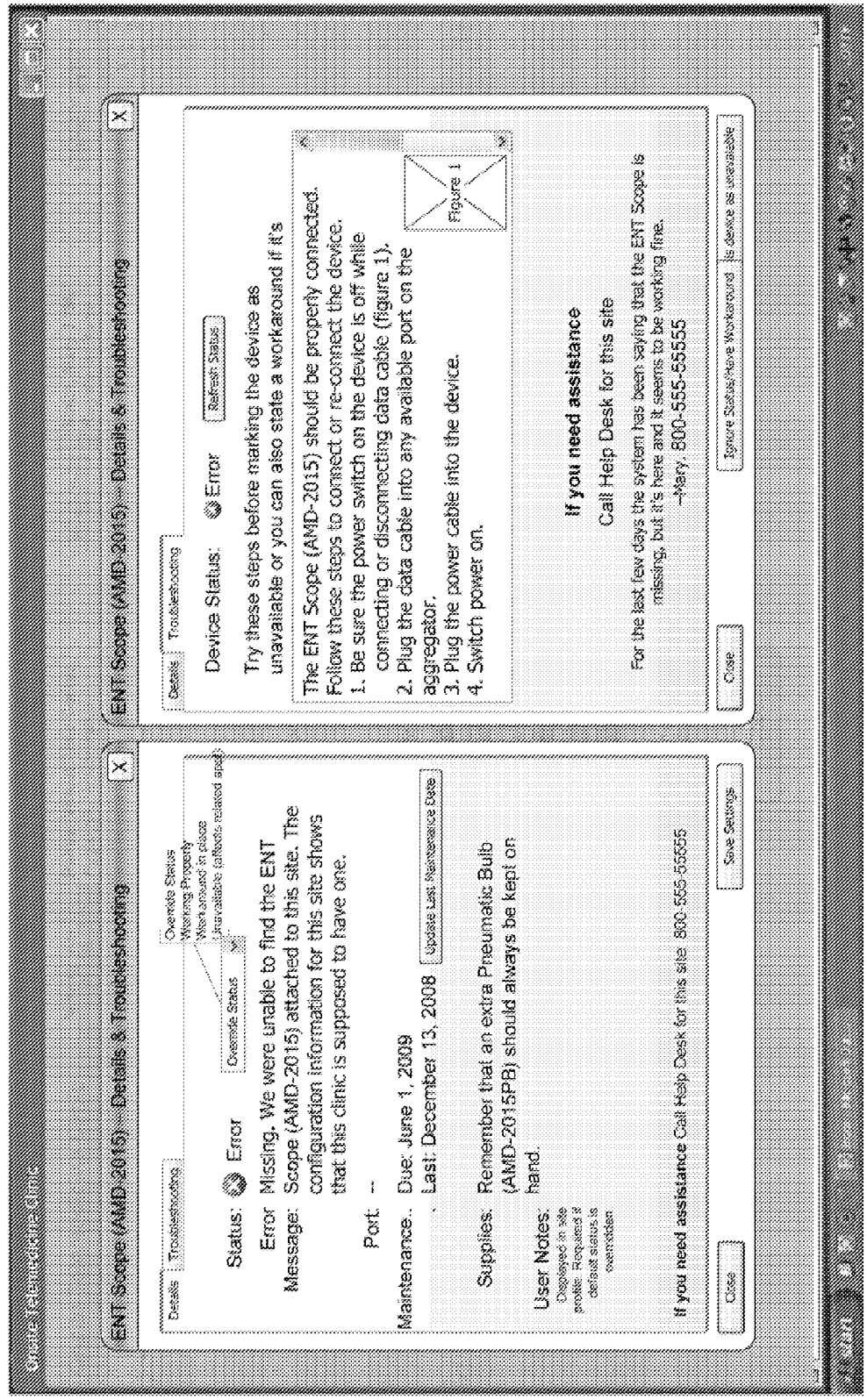
Figure 18:
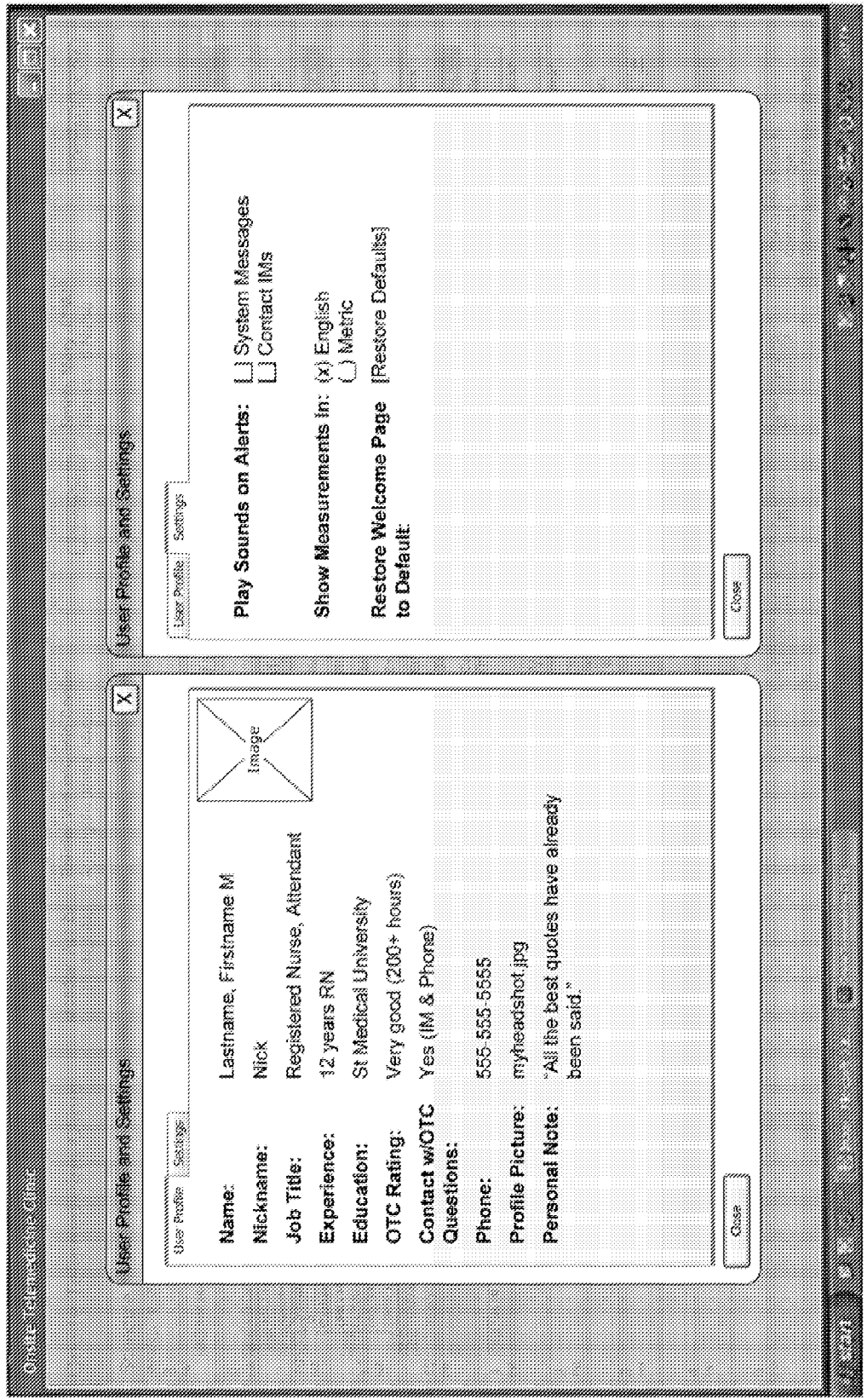
Figure 19:
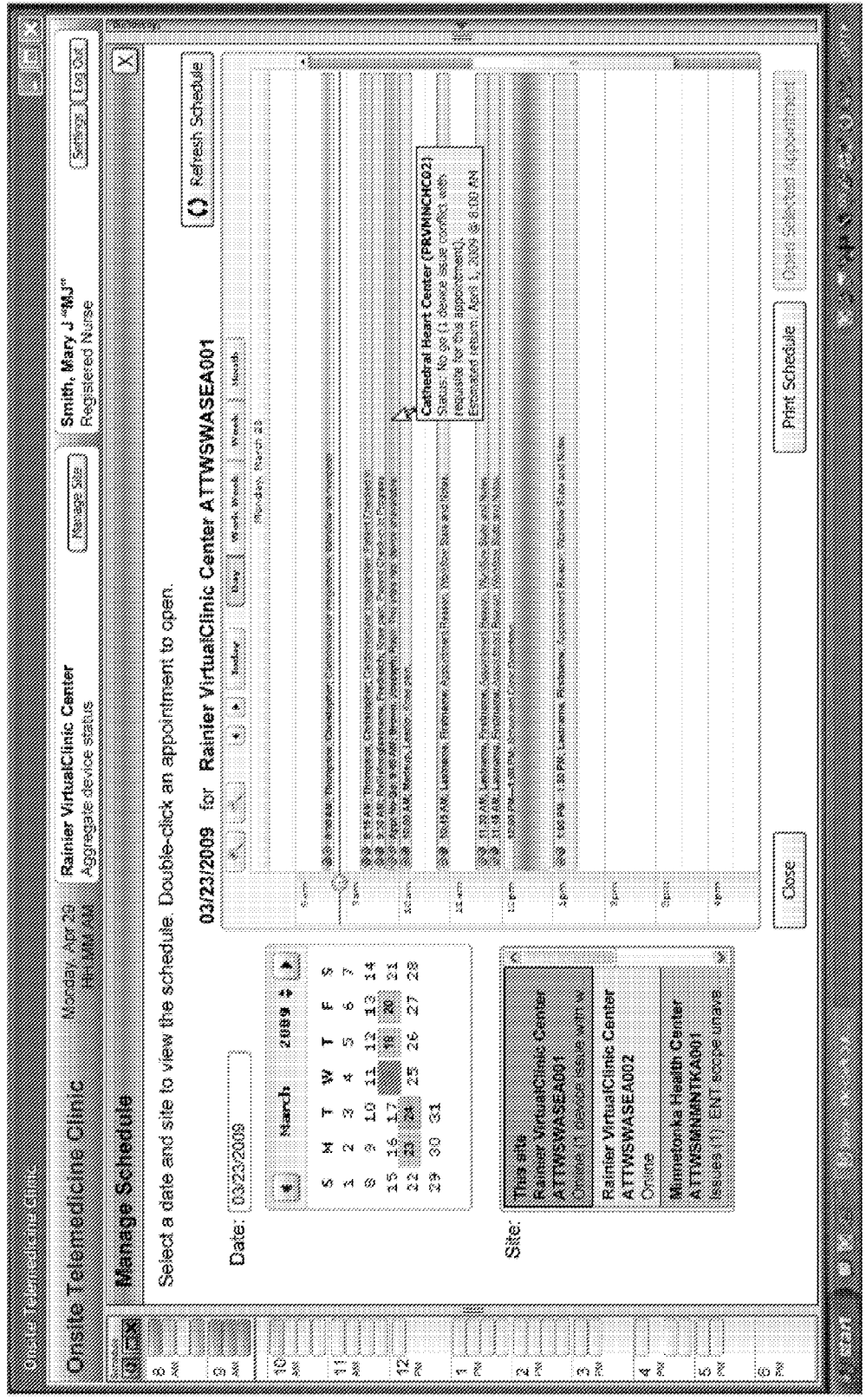
Figure 21:
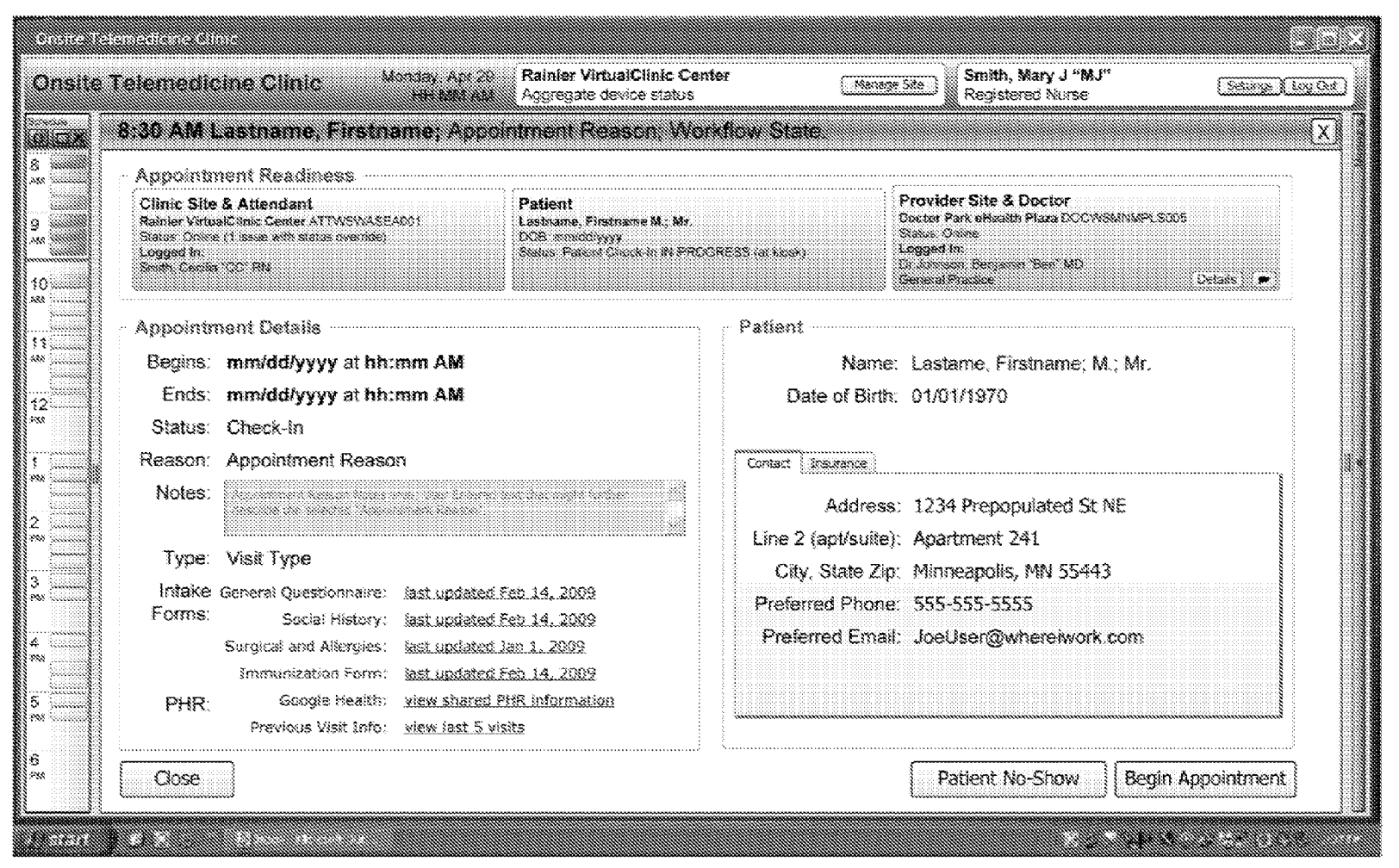
Figure 22:
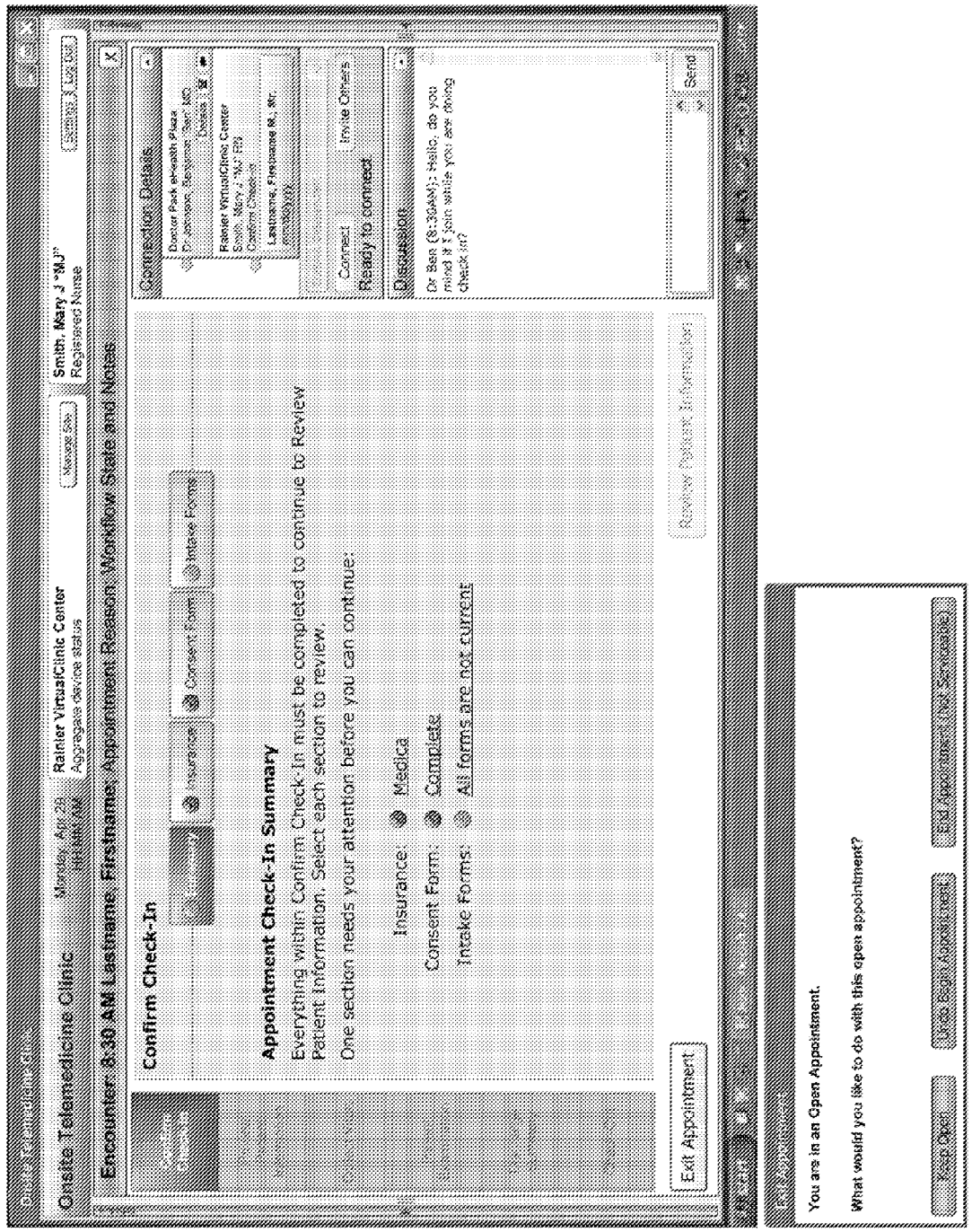
Figure 23:
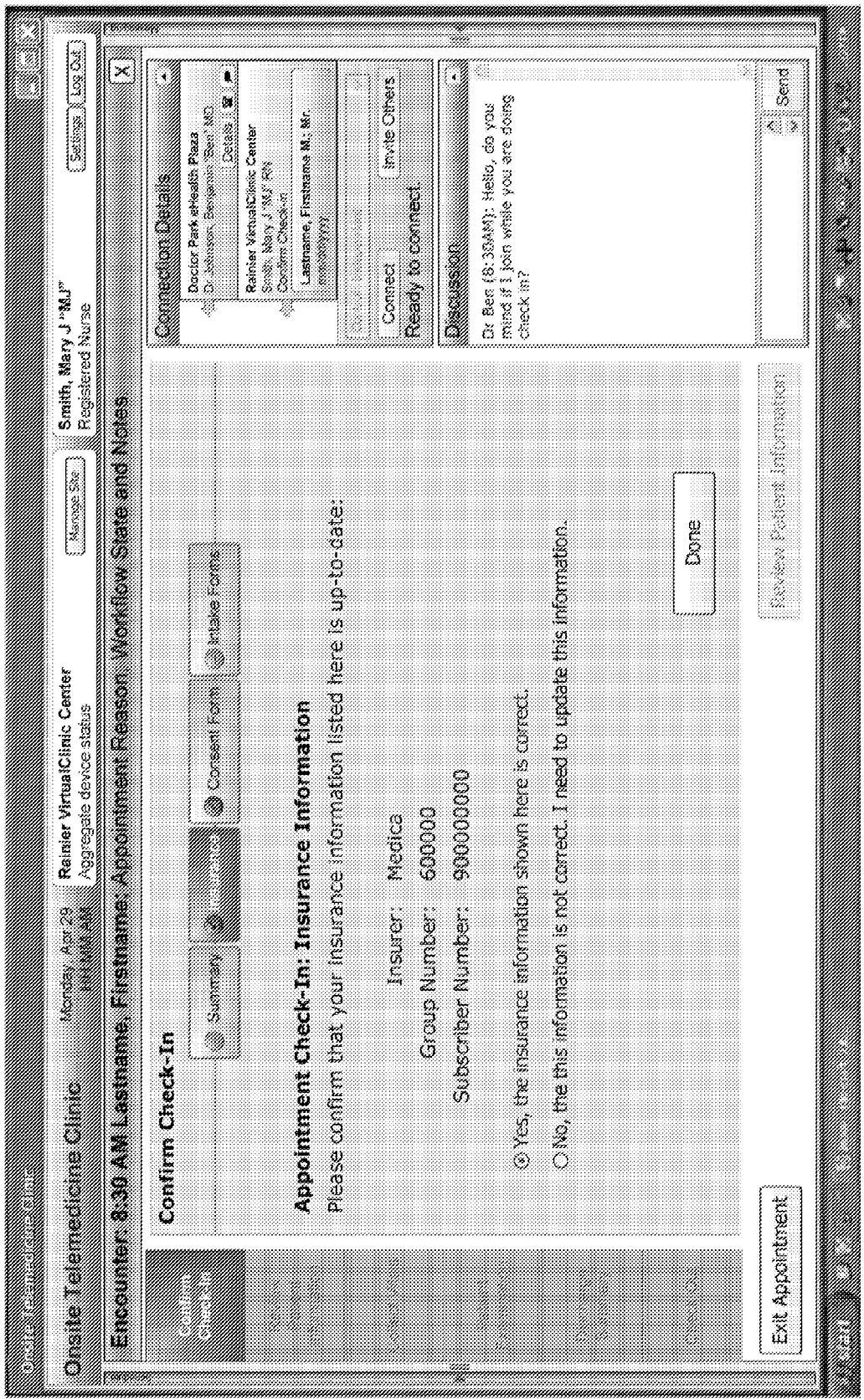
Figure 24:
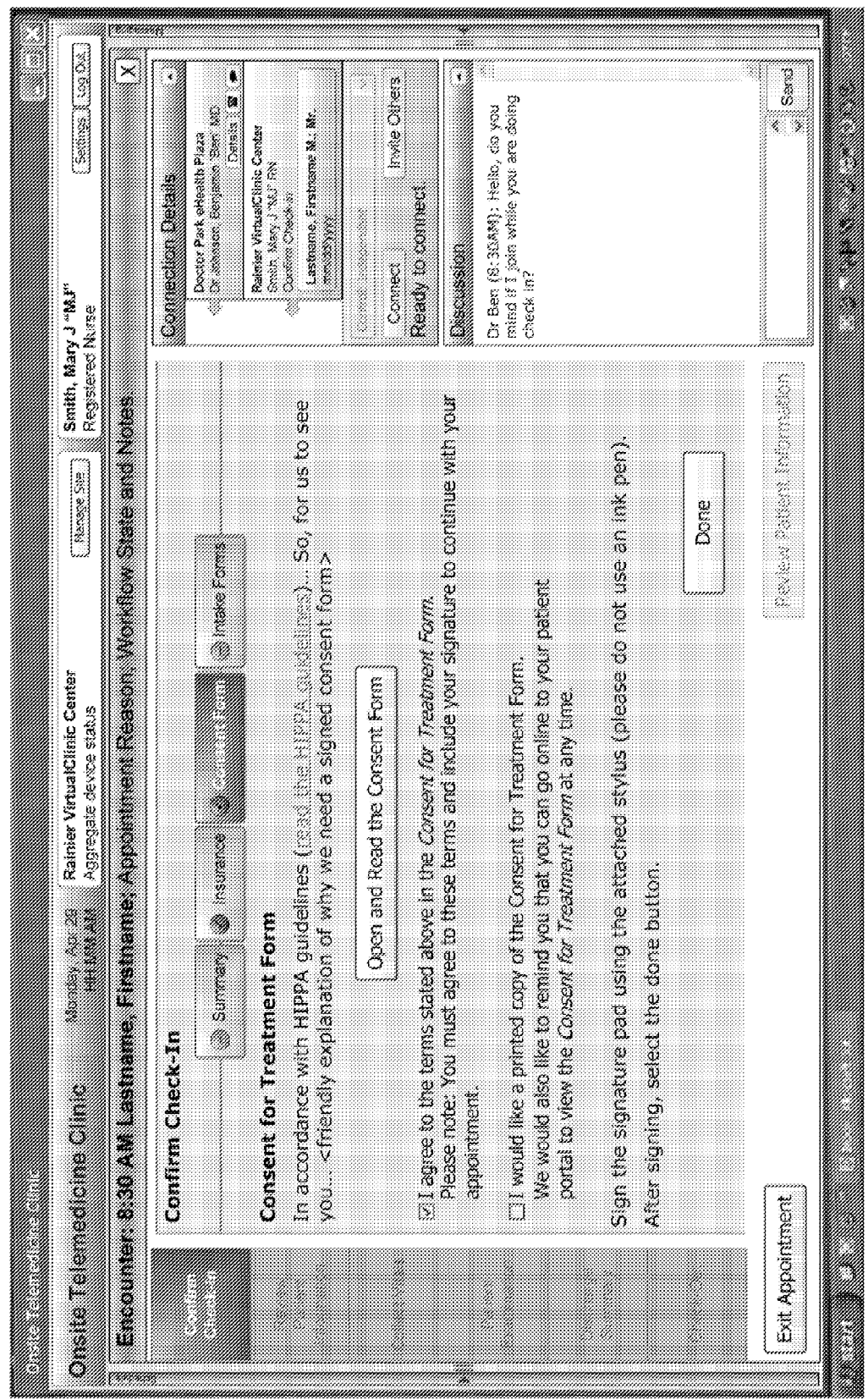
Figure 25:
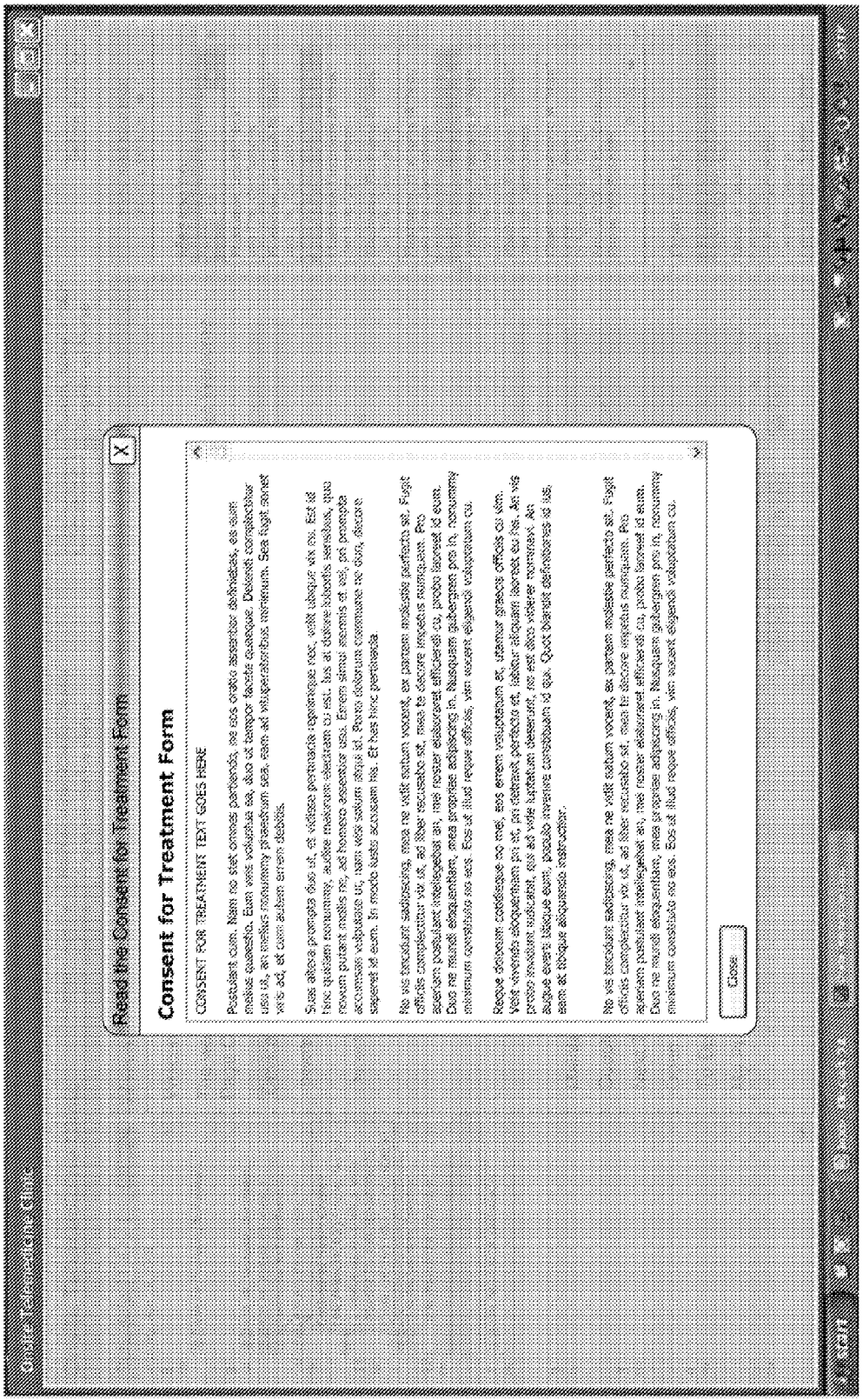
Figure 27:
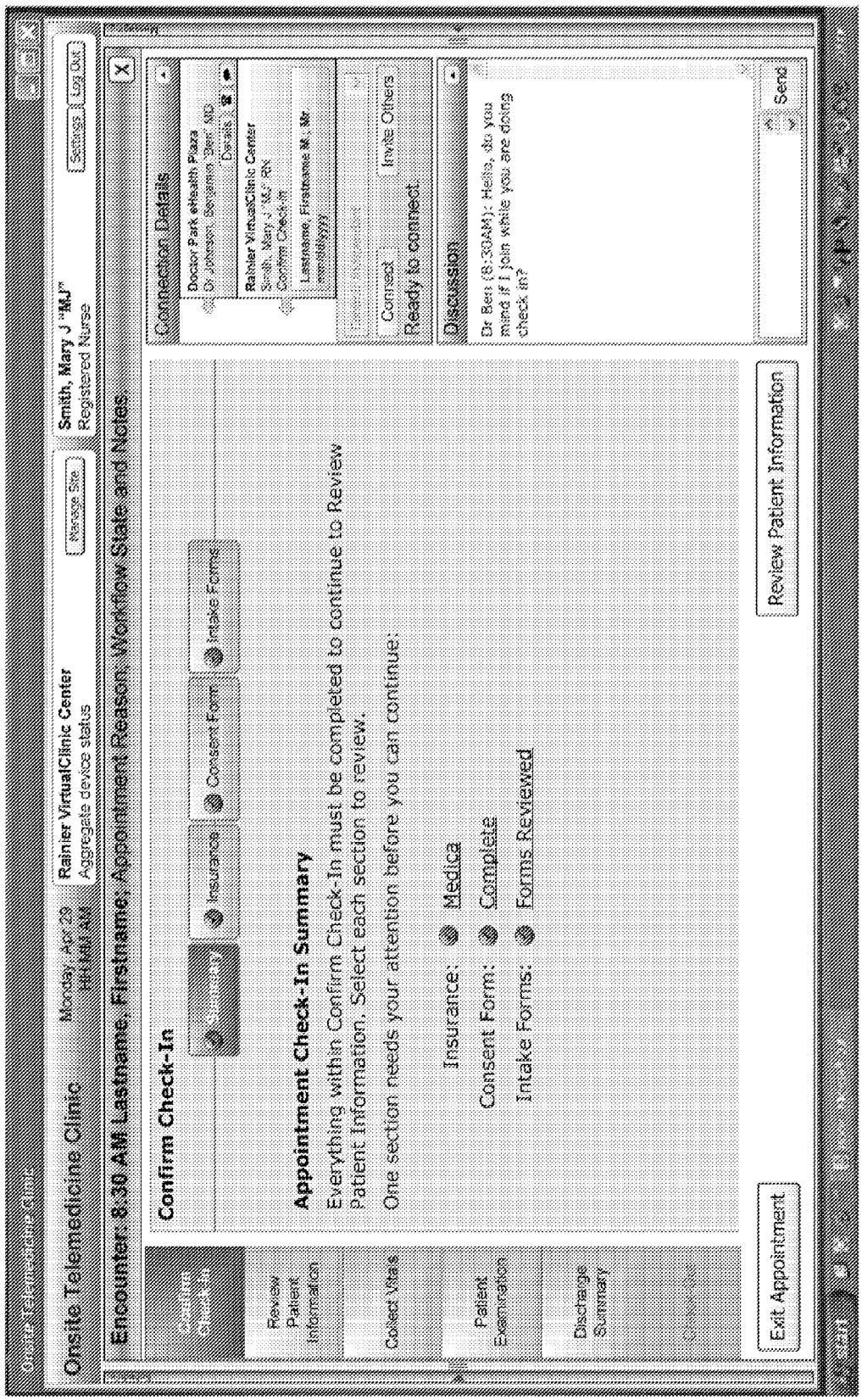
Figure 28:
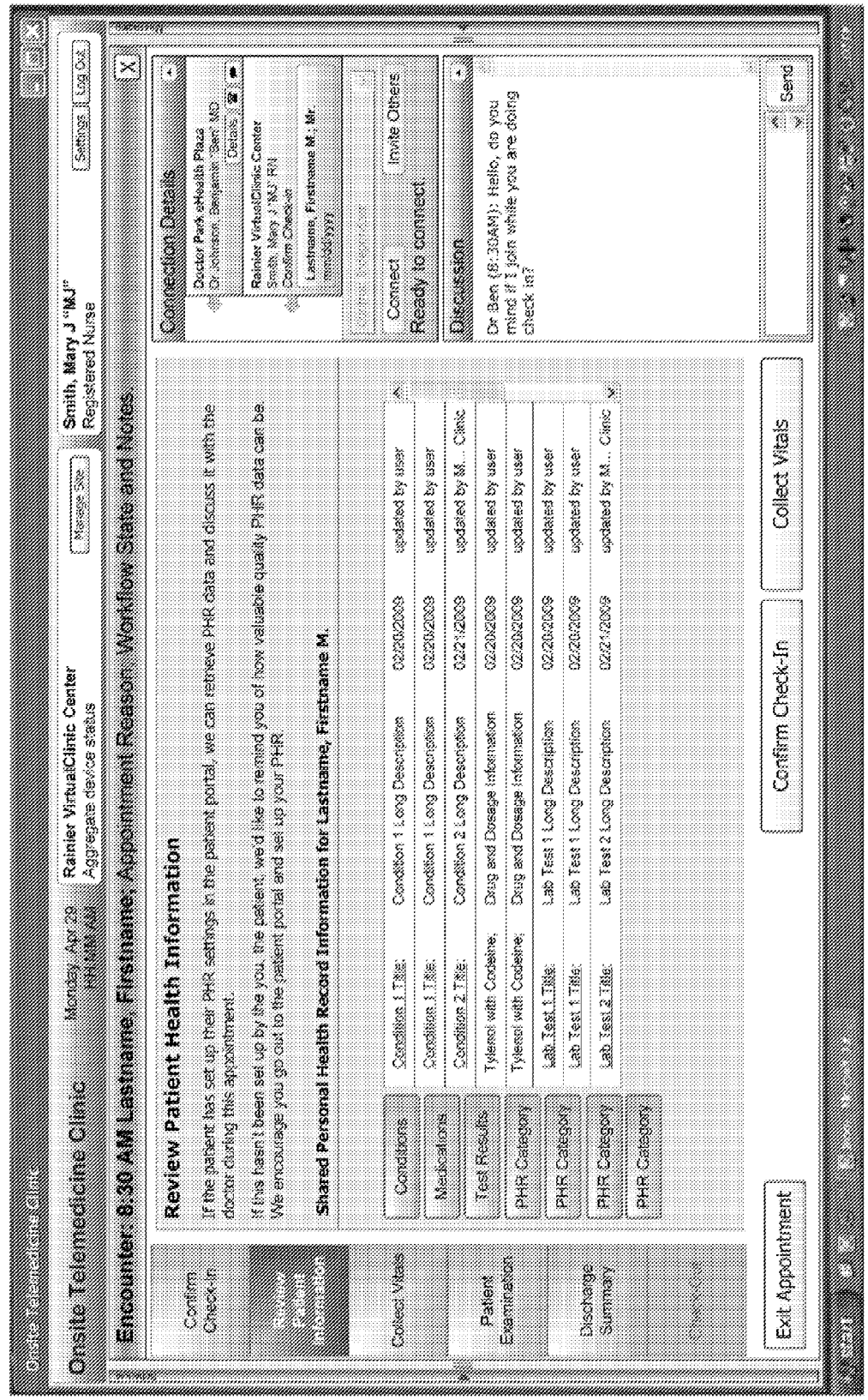
Figure 30:
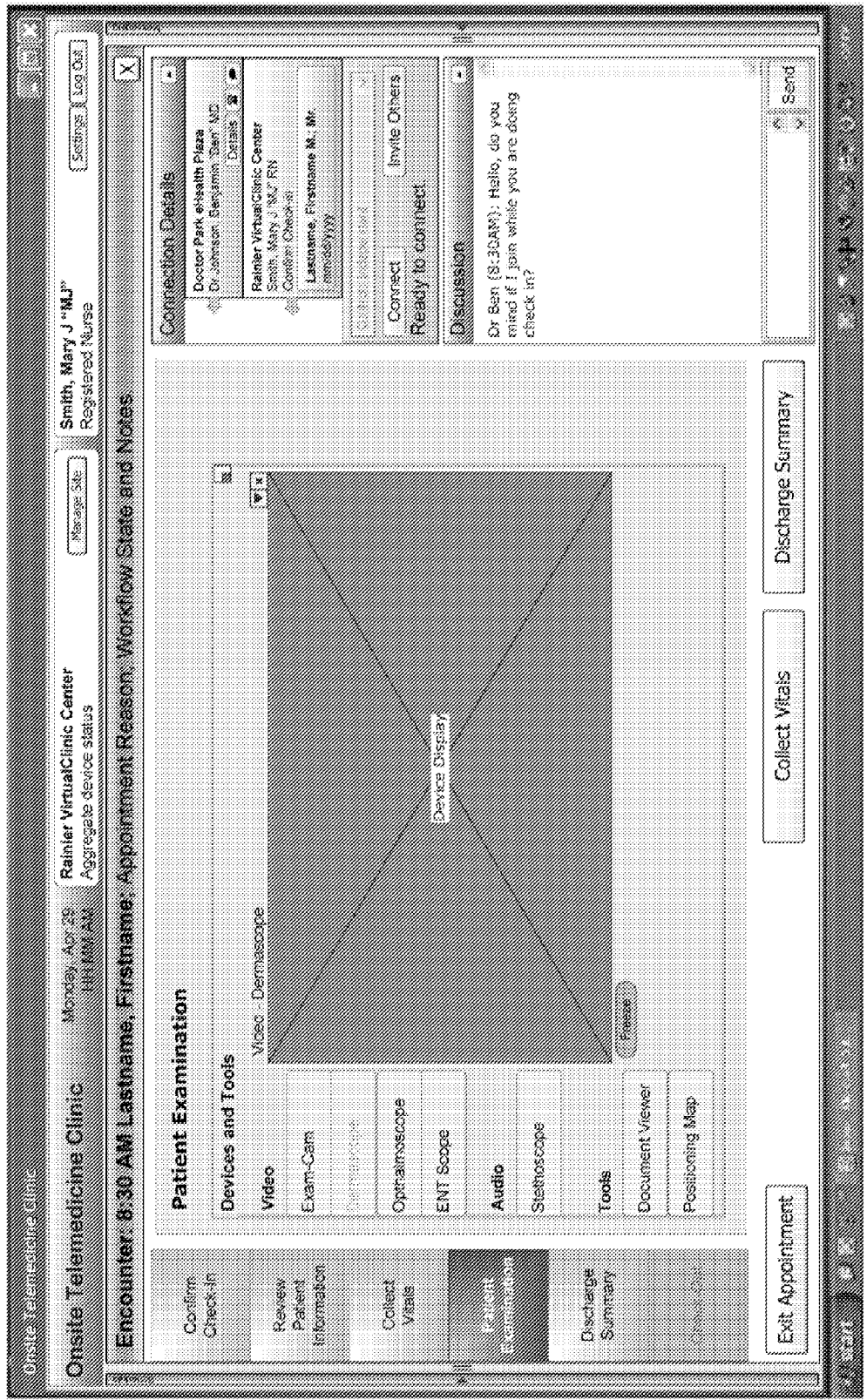
Figure 31:
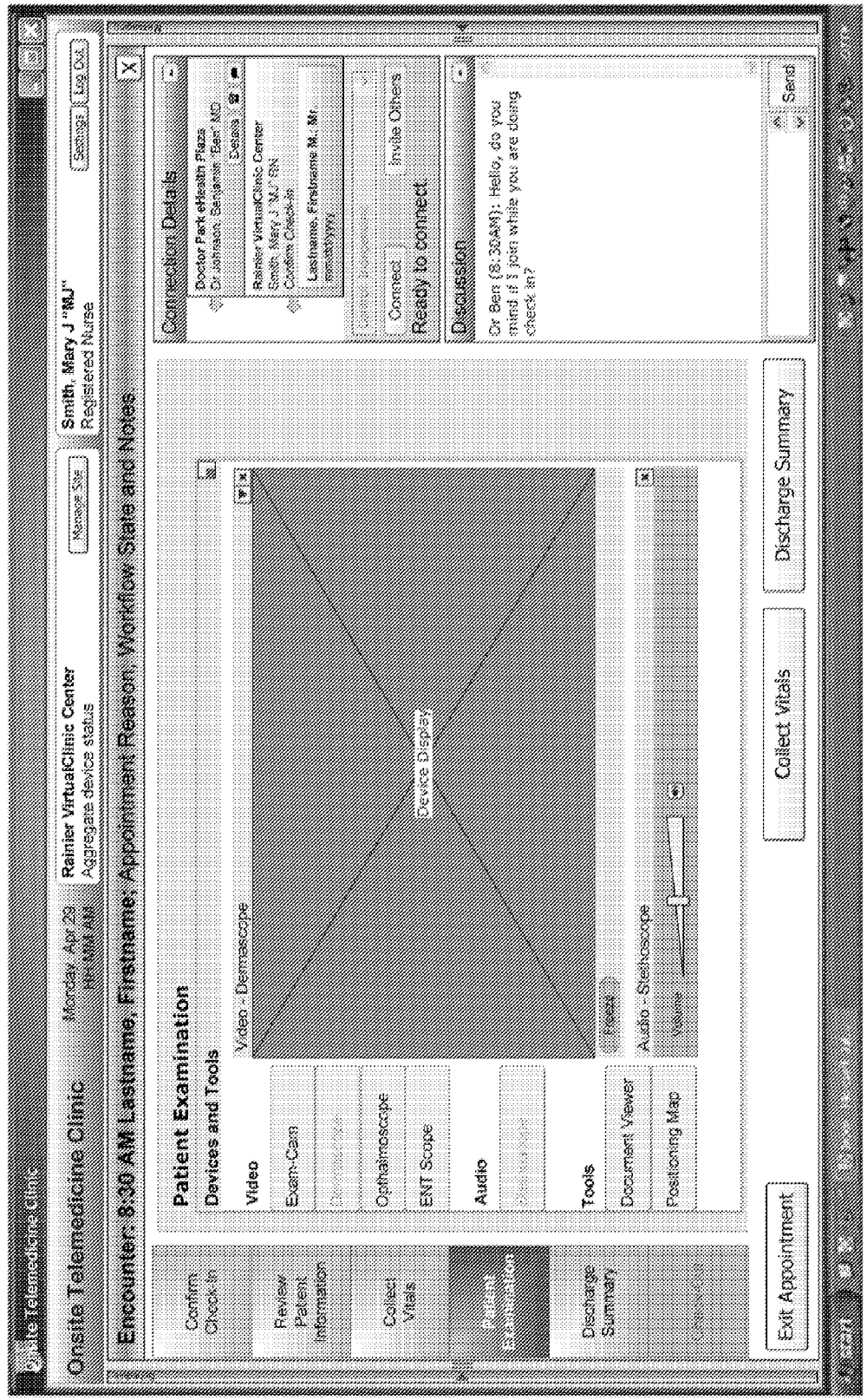
Figure 32:
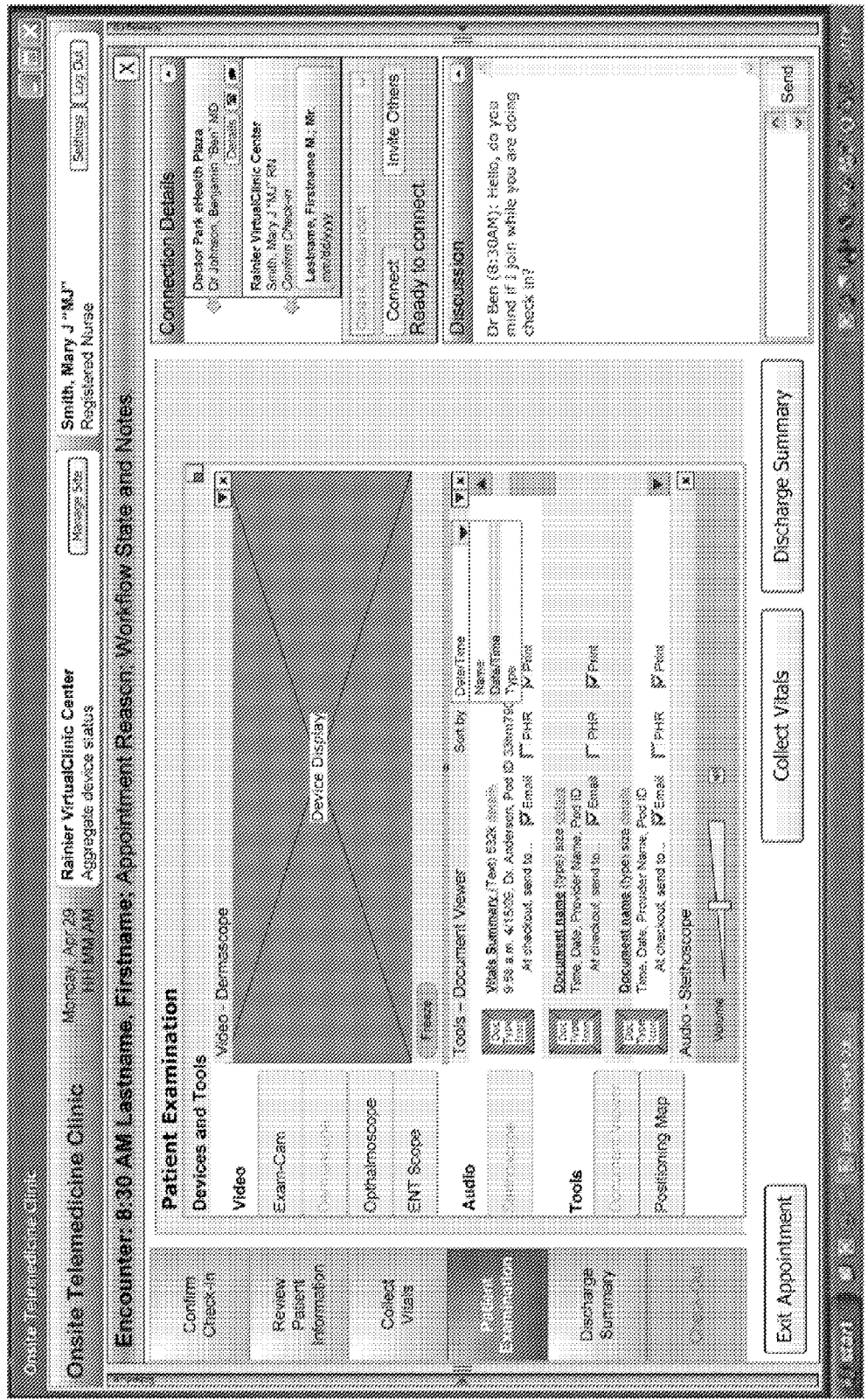
Figure 33:
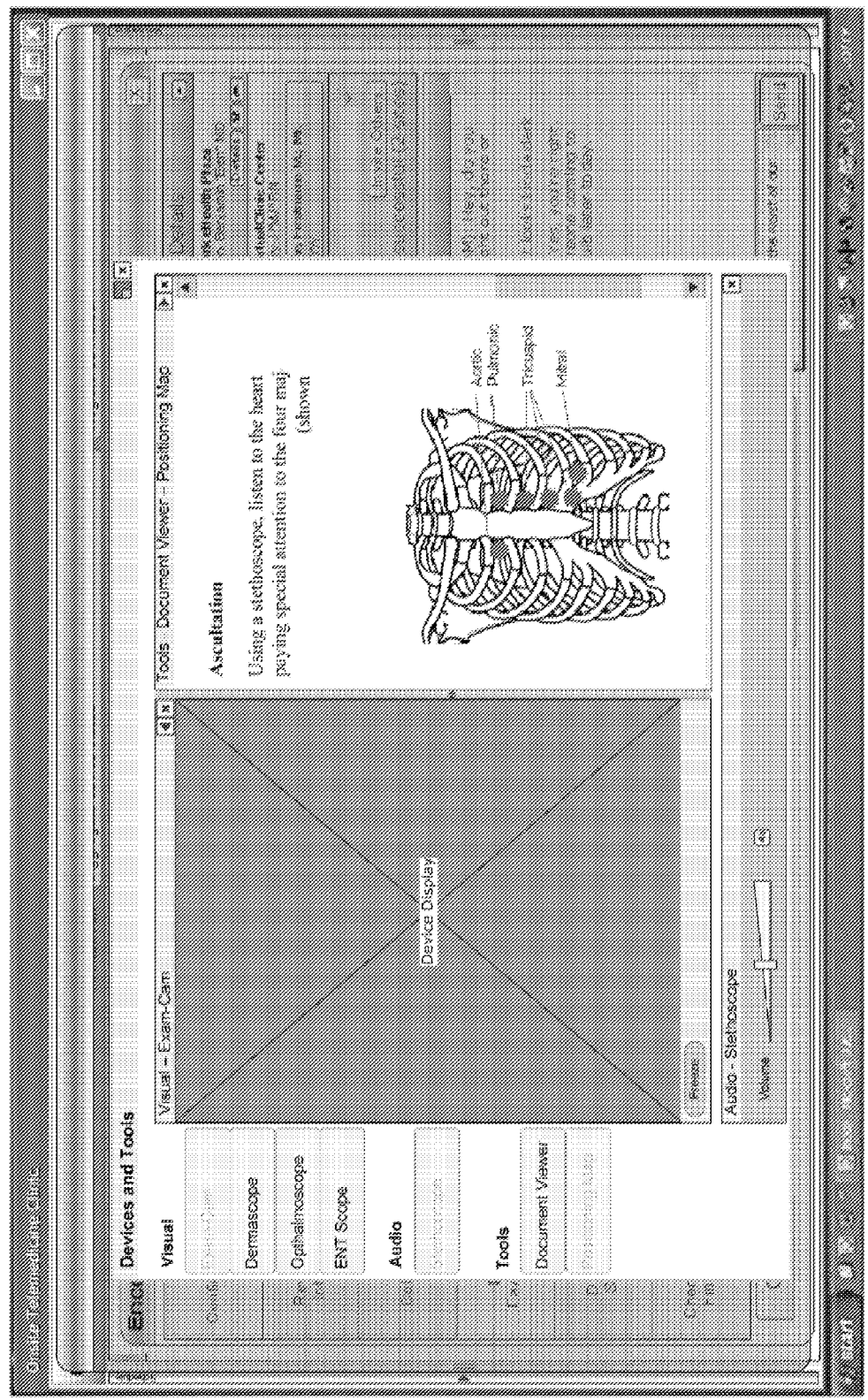
Figure 34:
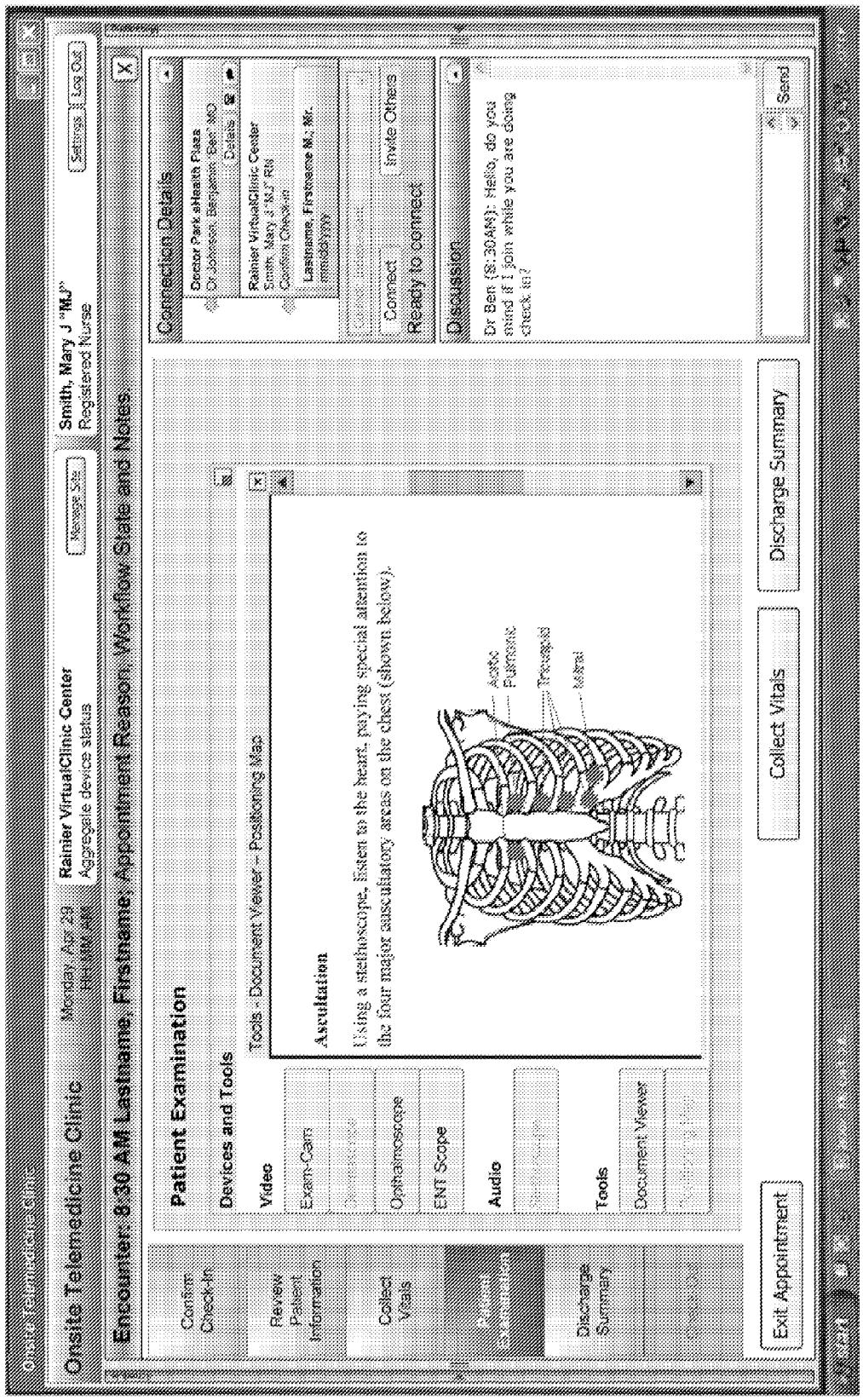
Figure 35:
Figure 36:
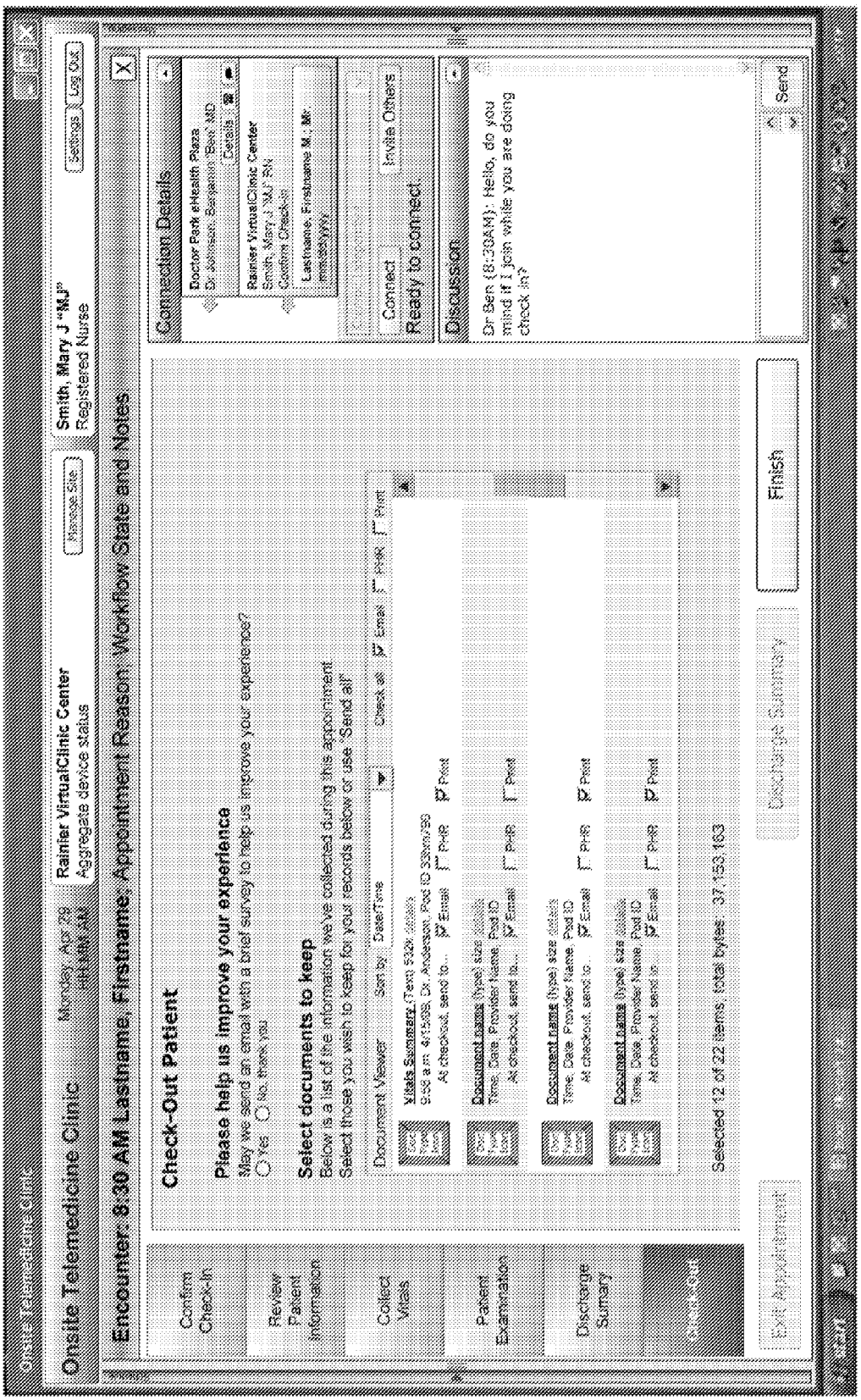
Figure 37:
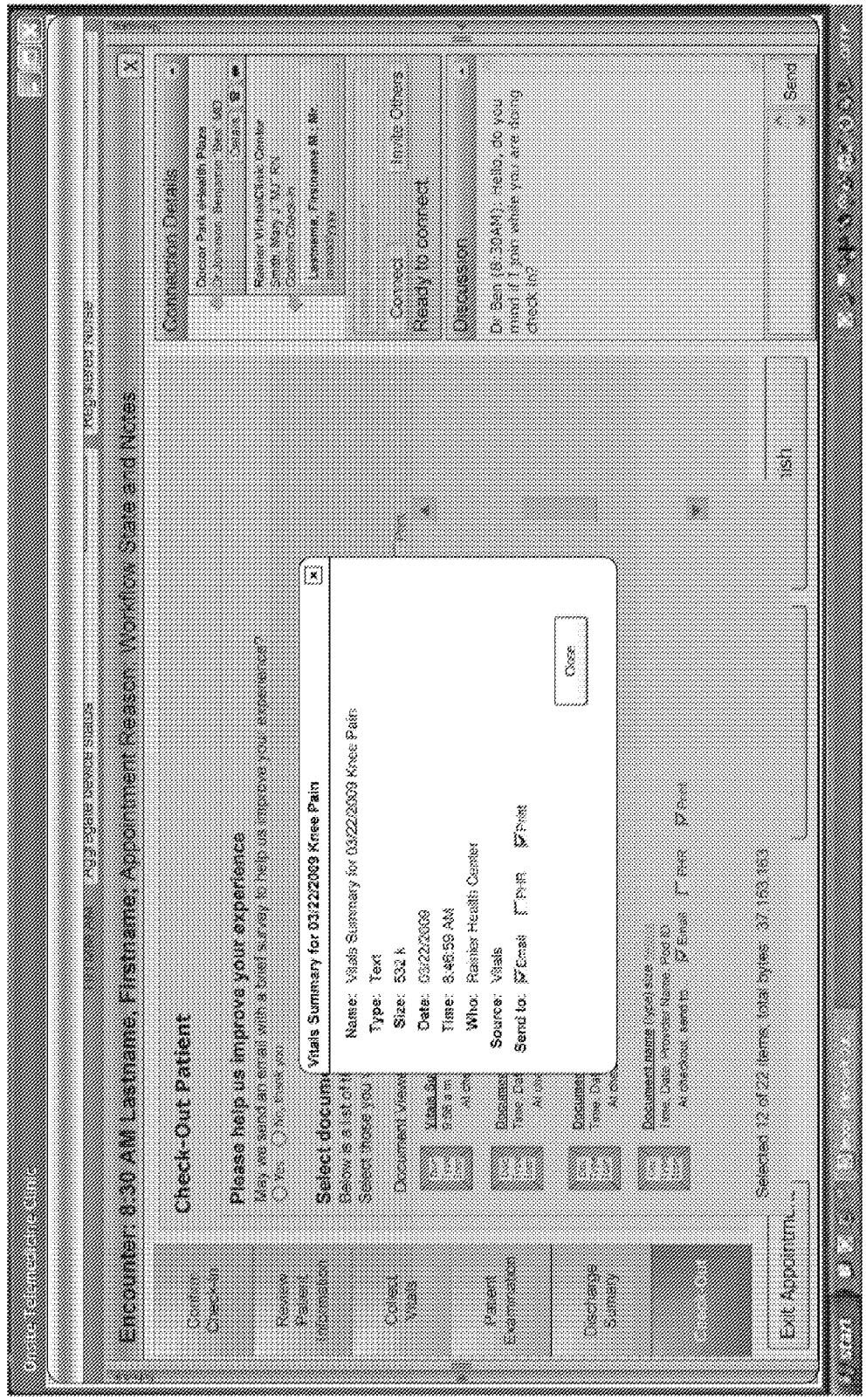
Figure 38:
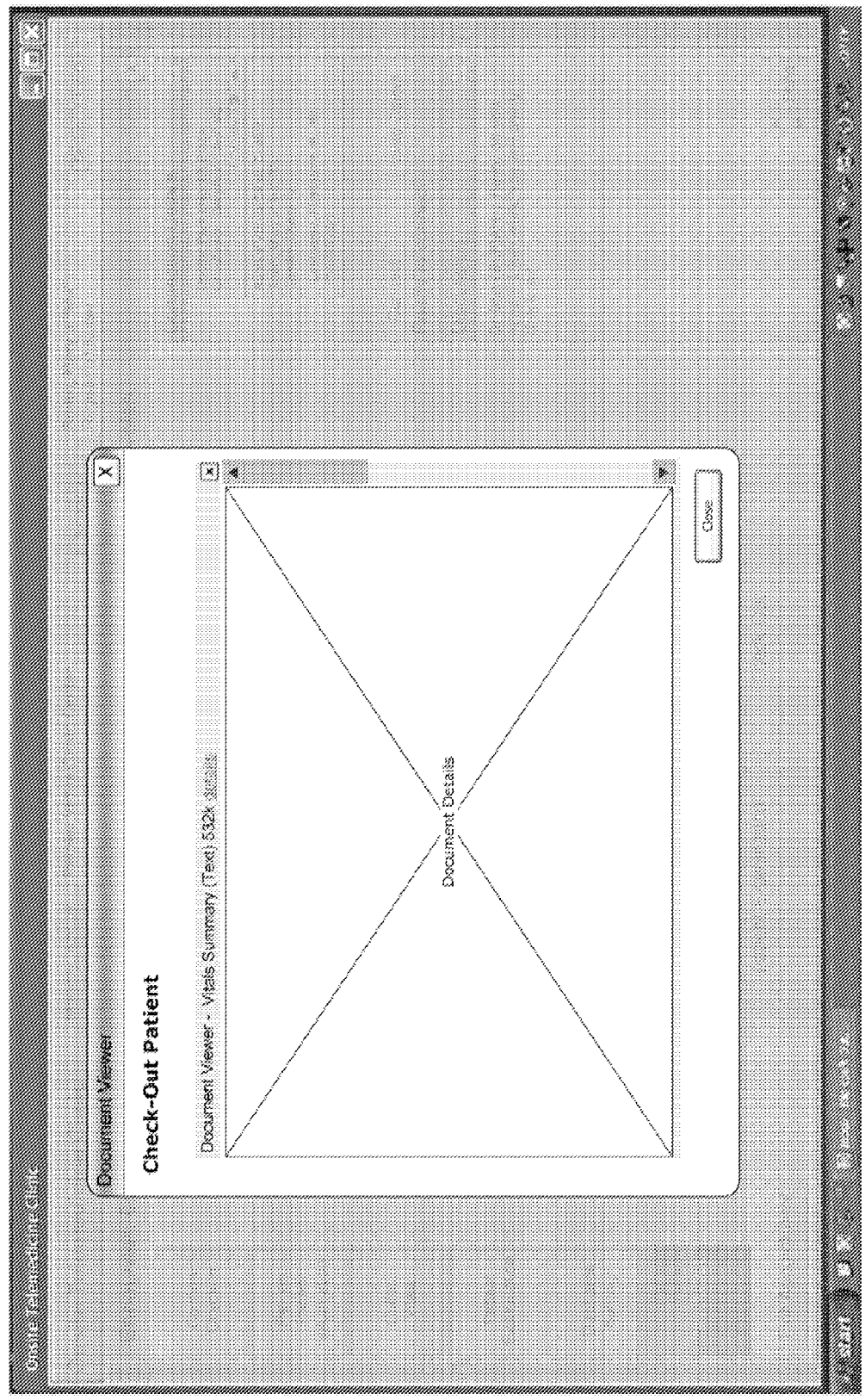
Figure 39:
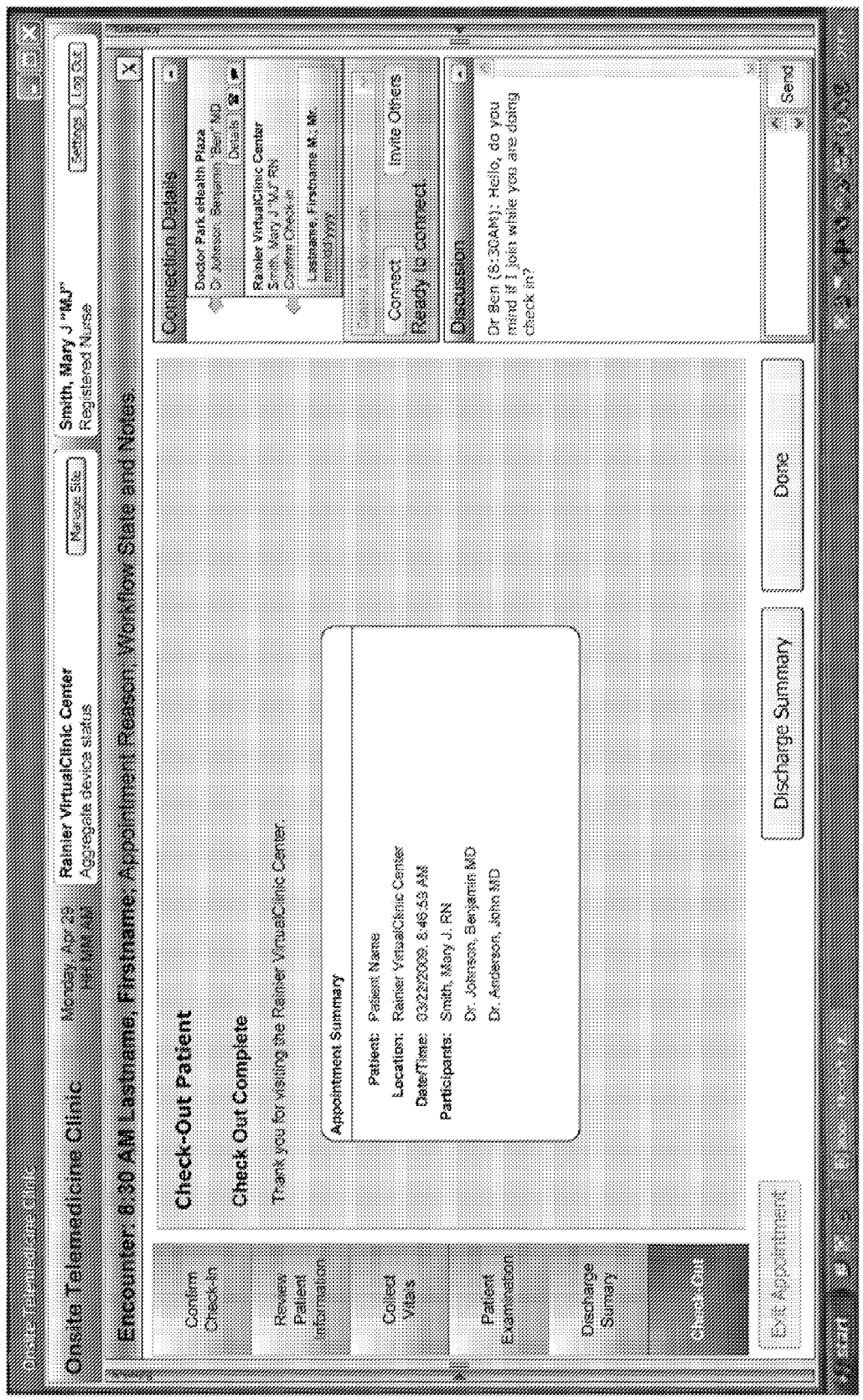

A nurse/attendant or provider may browse the day's schedule via browse schedule workflow 372, which may involve the workflow displaying the day's schedule and the status of each appointment (e.g., pending, canceled, checked-in, in process, and completed). See e.g., FIGS. 15-16 and 19-21. The workflow may display the status of the patient and the doctor and offer the user options for interacting with each appointment based on status. See e.g., FIG. 21. Interactions may be defined as workflows that lead the user through the steps required to process that appointment from start to finish. In addition to appointment status, the system may show the user any potential conflicts detected with the appointment's scheduled sites or with the predicted device needs of the appointment. For example, as a nurse/attendant views the schedule, if a scheduled provider site has been set to an inactive status due to a reported power outage or where an EKG machine is reporting an error status and there is a pending cardiology consult on the schedule, the attendant will see that a pending appointment has a conflict. For example, FIG. 17 depicts detail of an ENT scope error. Procedures to resolve these conflicts may involve a combination of automated scheduling responses, manual attempts to reschedule, cancelling of appointments, etc. Further, a central monitoring function may also be defined that will give a set of users the ability to see all scheduled events in the network. This central monitoring function may locate schedule conflicts and attempt to resolve them with minimal impact to the patient, attendant or provider. This function may also be monitoring network connectivity and usage to ensure that sufficient bandwidth is available and any site networking issues are addressed quickly. In addition, a user such as a nurse or attendant may customize their user account by selecting user settings. See e.g., FIG. 18.

A nurse/attendant and a patient may engage in a patient check-in workflow 373, which is a first step in the flow of an appointment. This function may be triggered by the physical arrival of the patient or by the nurse/attendant when the patient has not arrived within the appointment check-in window, for example. When the patient arrives, check in may initiate as a self check-in workflow or with the assistance of the attendant. For example, FIGS. 22-28 provide a series of screenshots depicting a workflow for a patient encounter in which the a patient engages in a check-in procedure. The patient may log into the portal and perform a set of tasks to authenticate themselves, provide insurance information, pay their co-pay, validate their health record (e.g., PHR)/health history and electronically sign any consent forms. Alternatively, a nurse/attendant may also perform/assist in the check-in workflow should the patient need or desire. The check-in workflow 373 may also be available to the patient via the web as a pre-check-in function that would allow them to complete most steps prior to arrival. The system may track the completeness of each step, perform a real time eligibility check (when possible) and process any financial transactions. Once complete, the patient is directed to the waiting room until the attendant is ready to begin the exam.

Once checked in, the nurse/attendant may review and verify the necessary forms are complete and that the forms have been properly distributed to those actors that will need them via review forms workflow 374. For example, this workflow may involve ensuring a patient's health history is available to physician and that consent forms are sent to provider practice. When possible, patient forms may be electronically sent to the physician back end systems. If no provider system is in use or integration is not present, faxing is performed. The physician may also have access to the electronic medical record (EMIR) available on the network 110 as a back end system option.

A nurse/attendant may review a patient's personal health records (PHR) via the review PHR workflow 375 to the extent allowed or complete. For example, where a patient grants access to their PHR all or a portion of the PHR is reviewed and/or updated via PHR workflow 375. Reviewing and updating may involve interfacing with third party PHR vendors (e.g., MyOptumHealth, GoogleHealth, HealthVault) through the network 110 health information exchange system in order to import and/or export PHR data from locations on the Internet. Alternatively, some level of information may be requested as part of the pre-encounter documentation process, and a completed heath history questionnaire may be minimally required.

A nurse/attendant and/or physician may view the patient visit data via patient visit data user interface workflow 376, in which a presentation layer delivers an aggregated collection of data on the patient. The data may be displayed on the patient side and physician side so that both may view, discuss and update during the encounter, and so that the physician may review the information prior to the encounter.

Figure 29:
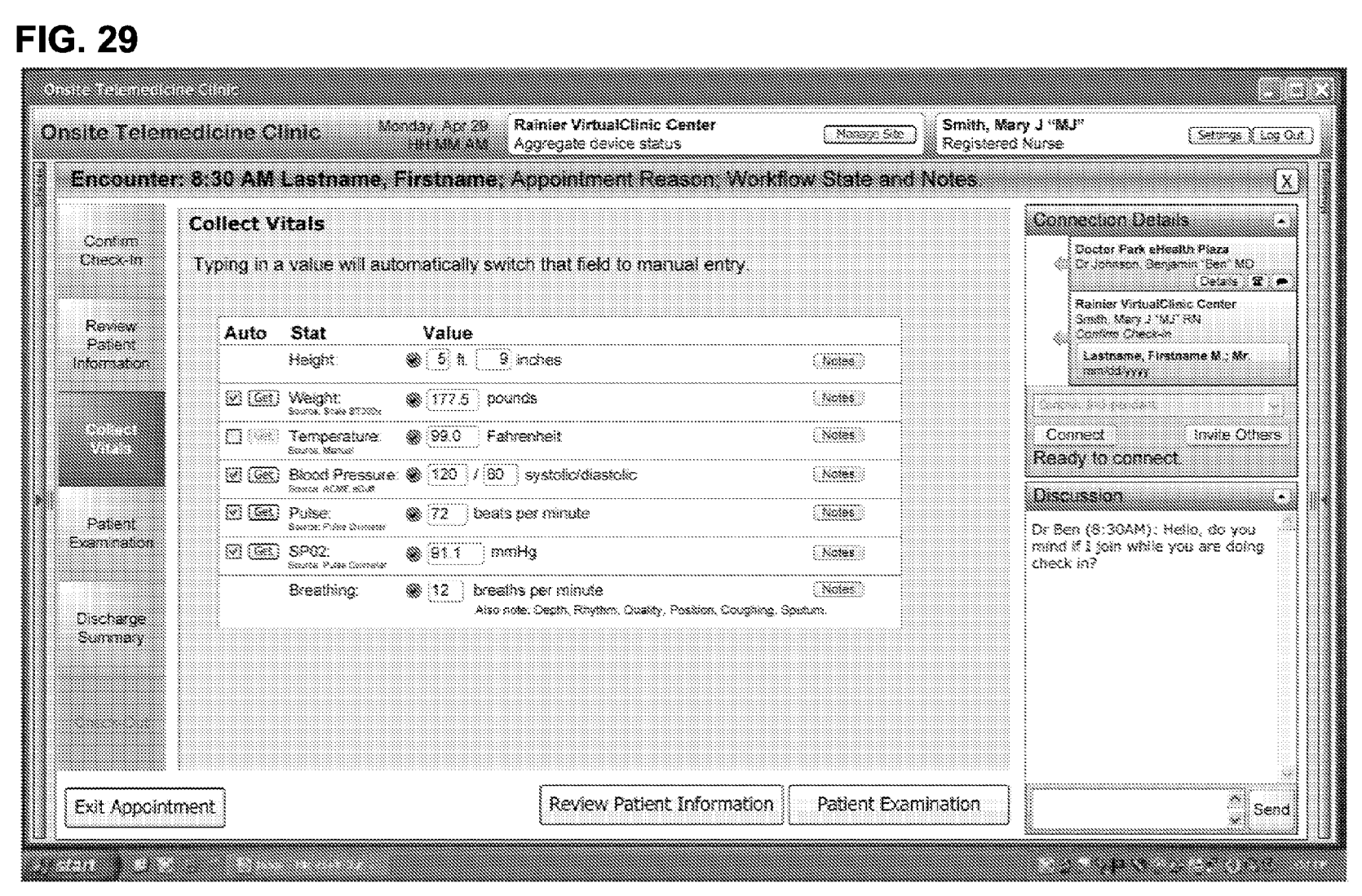

Once the patient has been checked in and the pre-encounter workflow is complete, the physician visit will commence, and the manage encounter workflow 380 may be primarily driven by the physician. Manage encounter workflow 380 allows the user to instrument and command medical devices 330 and the network components 315. The unified communication console 381 may create the user experience to present data and enable the interactions of the devices between the two sites. For example, unified communication console 381 may be presented on the portal that allows the physician and patient sides to interact under the control of the physician, and assists the attendant with managing the variety of telemetry devices in use during the exam. FIG. 29 depicts a screenshot of a workflow for collecting a patient's vital signs. The video conference link is also managed through the console, e.g., via a touch screen. For example, FIGS. 30-34 depict screenshots of a workflow that inter alia allows the physician to view a video of, listen to, take images of and give directions to the patient.

The conference engine interface 382 is responsible for managing the video conferencing connection. Platform 340 responds to commands from conference engine interface 382 to connect and disconnect the sessions. The commands will allow the console to create a seamless experience for the user when connecting video/audio and telemetry. For example, conference engine interface 382 may enable a nurse/attendant to browse various kiosks, various providers and to initiate an encounter in real time.

The telemetry display 383 provides a display for the variety of telemetry devices which may provide a user friendly interface to display data and to interact with the device's settings and output. The user interface may manage options such as: data retrieval, start/stop/playback type video functions, volume, white balancing routines and storage of the data/images captured.

The telemetry controls 384 control the specific calls that are made from the telemetry display to control the devices are contained in this part of the system. Telemetry controls 384 provides a layer of abstraction that will make the actual device independent from the telemetry display. That is, although a device type may change (e.g., different manufacturer), the function does not, and the display is unaffected by the swap.

The telemetry adaptor 385 in connection with platform 340 may manage the specific telemetry devices and the integration of that device to the telehealth communications network 110. The telemetry adaptor 385 may provide the specific interfaces to interact with the platform 340 and its devices, and may further insulate the user facing functions from any change in hardware or platform. According to certain implementations, the user may employ the telemetry display 383, controls 384 and adaptor 385 to command the medical devices in combination with device adaptor/aggregator 321. The telemetry display 383, its controls 384 and the adaptor 385 provide the interface to interact with platform services that abstract the capabilities of the medical devices. Accordingly, the user may employ the telemetry controls 384 to command the medical devices 330 with the aid of the telemetry adaptor 385.

At the conclusion of the medical exam, the post encounter initiation workflow 386 commences, which involves two main steps. First, a medical outcome may include one or more of: e-prescription, lab referral, specialist referral or discharge summary. Patients may receive a discharge summary generated by the physician that records the visit, diagnosis, specific outcomes and doctor's instructions. See e.g., FIG. 35. Second, outcomes may be generated from the physician's management system (EMR), which could be the EMR in use at their practice or the network-based EMR. When the outcomes have been communicated to the patient, the encounter ends and the session is terminated. At this point the physician site is free to engage in its next encounter.

The patient discharge workflow 387 enables the nurse/attendant to confirm the patient is provided with the materials from their physician and that the patient understands any instructions. See e.g., FIGS. 36-39. The nurse/attendant may conclude the visit in the network as the final step in the overall manage encounter workflow 380. At this point, the site is ready to initiate the next scheduled appointment.

Client-Side Communications

Telehealth communications network 110 seamlessly integrates various business processes in connection with telemetric devices and conferencing capabilities by communicatively coupling point-of-care sites with and care-dispensing sites and to enable on-demand healthcare.

Figure 4:
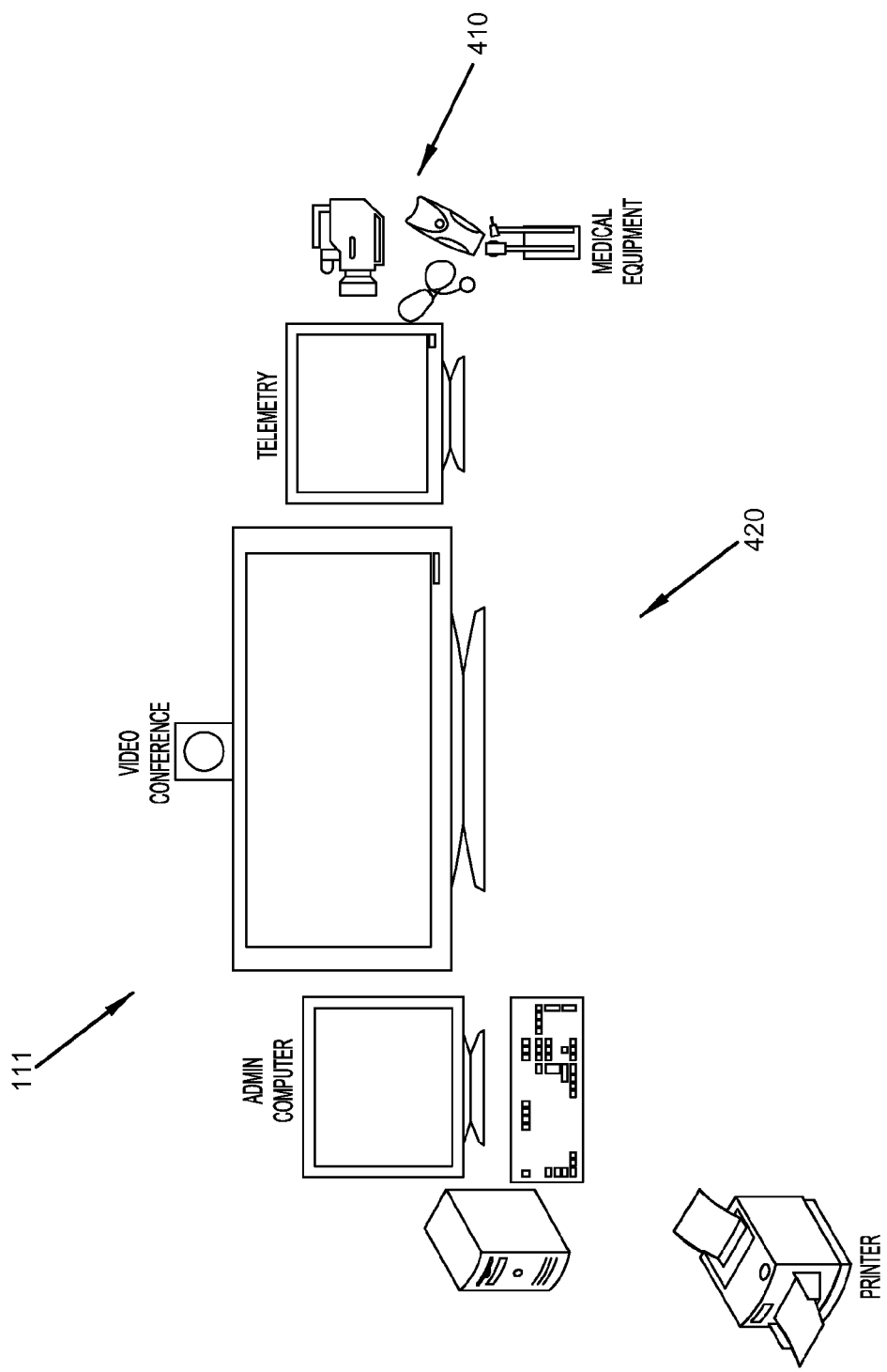
FIG. 4 illustrates the components of an integrated clinic facility that may be coupled to the telehealth communications network according to certain embodiments.

According to certain implementations, the communications network 110 is implemented client-side at a point-of-care site, and enables operators at the integrated clinic 111 to engage in a dynamic (e.g., on-demand) communication and collaboration with remotely located providers. FIG. 4 illustrates the components of an integrated clinic 111 coupled to the telehealth communications network 110. According to FIG. 4, an integrated clinic 111 may include medical equipment 410 (e.g., digital and non-digital medical diagnostic equipment and telemetry monitors) and unified communications and video conferencing 420 capabilities (e.g., patient computers, video conference monitors, a conference telephone, video cameras such as high-resolution cameras, administrative computer and monitor, a server, a printer, a server recorder/caching device, and a router) connected to the telehealth communications network 110. In some implementations, the clinic 111 may be provided with visually enhanced rooms that have audio and visual components installed therein. In further implementations, a clinic 111 may include a separate and private conferencing area, as well as an adjoining room with an attendant workstation and workspace. An integrated clinic 111 allows customers, patents and/or care givers to be simultaneously connected with providers for healthcare and wellness decisions. It will be understood that a clinic 111 may be any location accessible to a customer. For example, clinics may include health pods, kiosks or discrete locations set up with the medical apparatus, unified communications and video conference capabilities for the purpose of providing a customer location that allows the customer to telecommunicate with a provider located remotely. In another example, clinics may be a rented space, a doctor's office, a store front, a publicly accessible location, or any other location suitable for communicatively connecting a customer to a remotely located provider.

Figure 5:
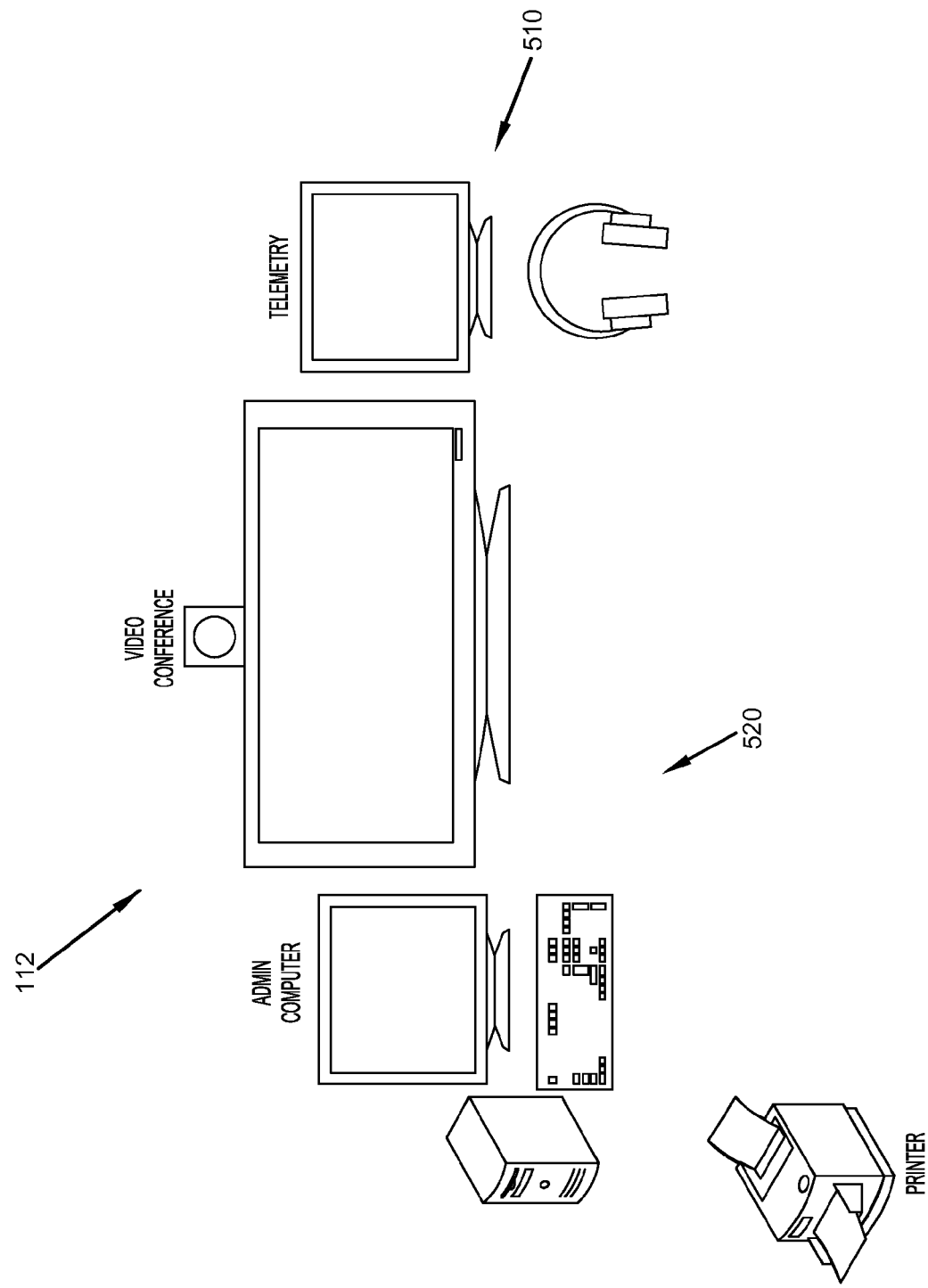
FIG. 5 illustrates the components of an integrated provider facility that may be coupled to the telehealth communications network according to certain embodiments.

Telehealth communications network 110 is further implemented client-side at a care-dispensing site, and enables providers to engage in dynamic communication with patients and nurses/attendants located remotely. FIG. 5 illustrates the components of an integrated provider facility 112 that may be coupled to the telehealth communications network 110 in order to communicatively connect providers remotely located from customers. For example, a provider facility 112 may include a telemetry station 510 and unified communications and video conferencing 520 capabilities (e.g., a computer, at least one video monitor (e.g., high-definition monitor), at least one video camera (e.g., high-resolution camera) and at least one audio interface) connected to the telehealth communications network. According to certain embodiments, a provider or group of providers, such as a group of physicians, may be stationed at the integrated provider facility 112 located at their principal place of business or at another location, and may make clinical, diagnostic and treatment decisions for a remotely located customer upon interacting with the remotely located customer via a telehealth communications network 110. In addition, a provider may have access to a customer's electronic medical records and may be able to review and/or observe tests performed on the customer in real-time.

Care givers (e.g., clergy, family members, non-profit third parties, case managers, financial advisors, health plan representatives, pharmacists, and other interested parties) may access one or more care providers in one setting by utilizing the communications network 110 via a third party location or access point 113 (see FIG. 3A), for example. A third party facility may be coupled to the telehealth communications network via the Internet and may include video conferencing components including a telephone, a computer and a monitor. Providing a third party access point 113 may enable customers and interested third parties to access any combination of providers at multiple locations at the same time.

Server-Side Communications

Figure 6A:
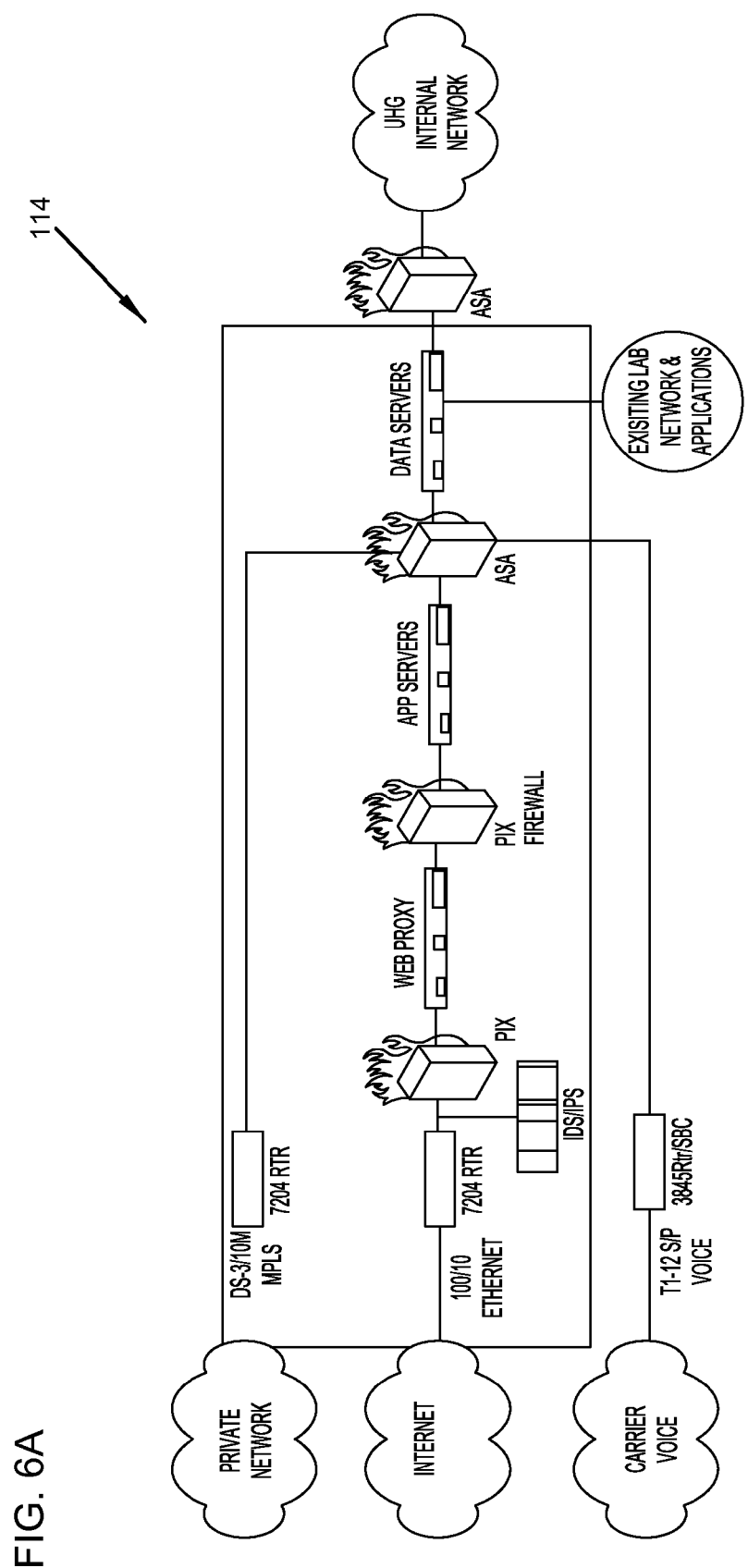
FIG. 6A illustrates the components of centrally managed and integrated data center that may form a portion of the telehealth communications network according to certain embodiments.

FIG. 6A illustrates the components of a centrally managed and integrated data center 114 in telehealth communications network 110, according to certain embodiments. The physical components of the data center 114 may include databases, servers and routers for connecting the data center to a private clinic network, the Internet, and voice and video carriers. Data residing on the databases in the data center may include client, provider, and clinic information collected from multiple sources internal to and external from the network. In some implementations, the data center 114 may be separated from the telehealth communications network 110 by firewalls and security components.

Figure 6B:
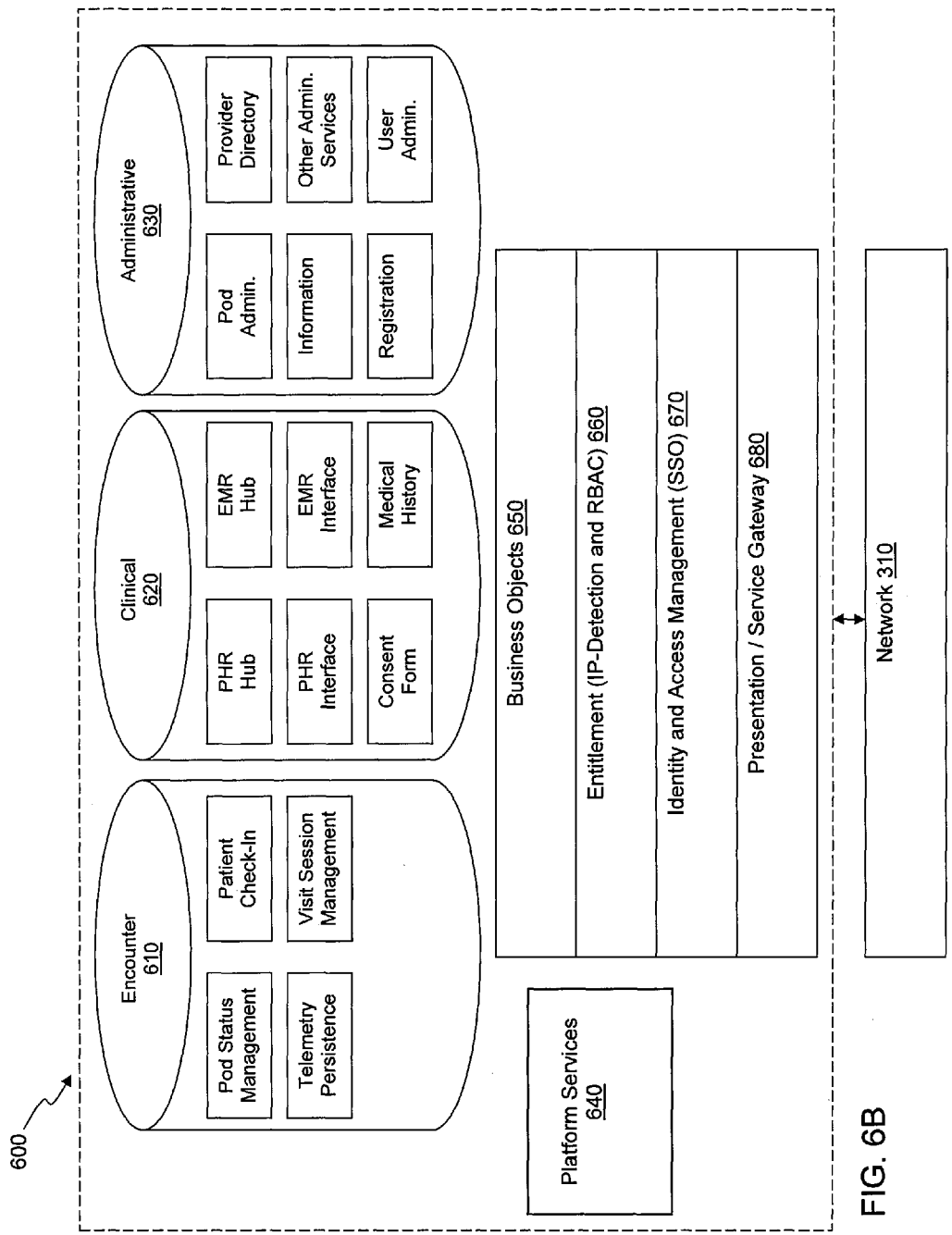
FIG. 6B illustrates a server infrastructure coupled to a network, which supports multiple clients and provides three sets of capabilities including: encounter, clinical and administrative server modules.

Accordingly, telehealth communications network 110, in combination with integrated data center 114, may implement a server module for providing common services to all clients and users. FIG. 6B illustrates a server infrastructure 600 coupled to network 310, which supports the multiple clients and provides three sets of capabilities including: encounter 610, clinical 620 and administrative 630 server modules. Encounter server module 610 provides capabilities for patient and provider encounters and interactions including clinic, pod or kiosk status management, telemetry persistence, patient check-in and visit session management. Clinical server module 620 provides workflows pertaining to the clinical aspects of an encounter such as pre- and post-encounter formalities including retrieval, dispatch, updating and maintenance of patient and electronic health records via PHR and EMR hubs and interfaces, procurement and retrieval of consent forms, and accessing medical histories. Administrative server module 630 provides administrative workflows pertaining to managing the overall operations vis-à-vis managing pods, providers, information (e.g., directories), other administrative services (e.g., education services), registration and user administration.

According to certain implementations, the central server 600, via encounter server module 610, administers encounter workflows so that, during an encounter between a patient and the provider, resources or artifacts that the entities consume or produce are securely managed for safe retrieval. Pod management status workflows enable management of the schedule and status of the clinic/kiosks and/or pods, which for example, dynamically monitor the status of the pods so their uptime can be managed. Server-side workflows support the check-in process of a patient. Telemetry persistence workflows manage the storage of medical readings over the duration of the encounter (e.g., short-terms and long-term management of telemetry data). Visit session management server-side workflows track and support sessions between the patient and the provider. For example, the number of concurrent sessions underway, the amount of data exchanged, the bandwidth consumed, and lost and restored connections are tracked using visit session management workflows. Visit session management workflows may also collect data for accounting purposes so that, for example, a kiosk supporter or vendor can verify utilization by reviewing network bandwidth use, for example. In another example, a patient can verify a patient physically checked-in at the kiosk for compliance purposes.

Clinical server 620 may host an EMR hub, which serve as a gateway to EMR systems from which doctors maintain their records. EMR hub may provide access to EMR vendors (e.g., Epic, Siemens, GE, e-Clinicalworks) that implement health information exchanges. Network 310, via PHR interface, for example, may establish trust with a vendor portal, and a physician or provider may access the telehealth communications network 110 via operating console 350. For example, a physician may grant permission to share their EMR record with network 310 by accessing operating console 350 via a website, where the network sends a message to the physician in order to establish connectivity. The network may be further configured to receive communications from the EMR vendor in order to receive the physician's EMRs.

Clinical server 620 may also host PHR hub, serving as a gateway to PHR websites (e.g., MyOptumHealth, GoogleHealth, HealthVault), which hosts data that is controlled by the patient. Nurse/attendees and patients may access a PHR interface, for example, in order obtain/grant access to the patient's vital sign, height, weight and other medical data in the PHR. For example, a patient may send a message to their PHR website indicating they agree to share their PHR with the network. In some implementations, PHR access may be granted by the patient as part of a scheduling workflow. Alternatively, the patient may grant PHR access upon patient check-in, or as a pre-check-in process. In instances where the patient does not have a PHR, they may be instructed to select a PHR website and create one, and access to the newly created PHR may be granted by the patient for utilization by nurse/attendants and physicians.

EMR and PHR records may be updated through PHR and EMR interfaces hosted on clinical server 620. For example, throughout an encounter, patient vital signs may be collected and uploaded to the physician's EMR from the EMR interface. In some instances, a network-based EMR is active on the system during the patient encounter. The network-based EMR may be provided to the physician's management system where their EMR is updated. A PHR may be updated with a discharge summary generated by the physician that records the visit, diagnosis, specific outcomes and doctor's instructions from the PHR interface. For example, during or after a post encounter workflow 386 or patient discharge workflow 387, for example, a nurse/attendant may access the PHR interface and export the session data to the PHR. In instances where a PHR is not available, data generated during the session may be purged, or may be provided directly to the patient as part of the post encounter or discharge workflows.

Central server 600 further includes platform services 640 and capabilities, business objects 650, entitlement capabilities 660, identity and access management capabilities 670, and presentation and service gateway capabilities 680. Platform services 640 provide management and monitoring support for the operational support of the platform 340 at the client side. In a further example, entitlement capabilities 650 and identity and access management capabilities track the identities, roles, entitlements, workflows, artifacts and other components related to implementing a number of concurrent sessions between patients and providers.

As described, the telehealth communications network 110 may implement business processes for facilitating storage and sharing of customer and provider information throughout the network. In particular, including data entry, receipt and storage means (e.g., computers, keyboards, touch pads or screens, scanners, voice, text and/or image recognition software and/or hardware, means for receiving data from other sources, e.g., wired or wireless network connections, and databases for storing data) enables users of the telehealth communications network 110 to retrieve, create, store and export consolidated electronic medical records (EMRs) and patient health records (PHRs) for customers, and to create and store profiles for providers.

Figure 7:
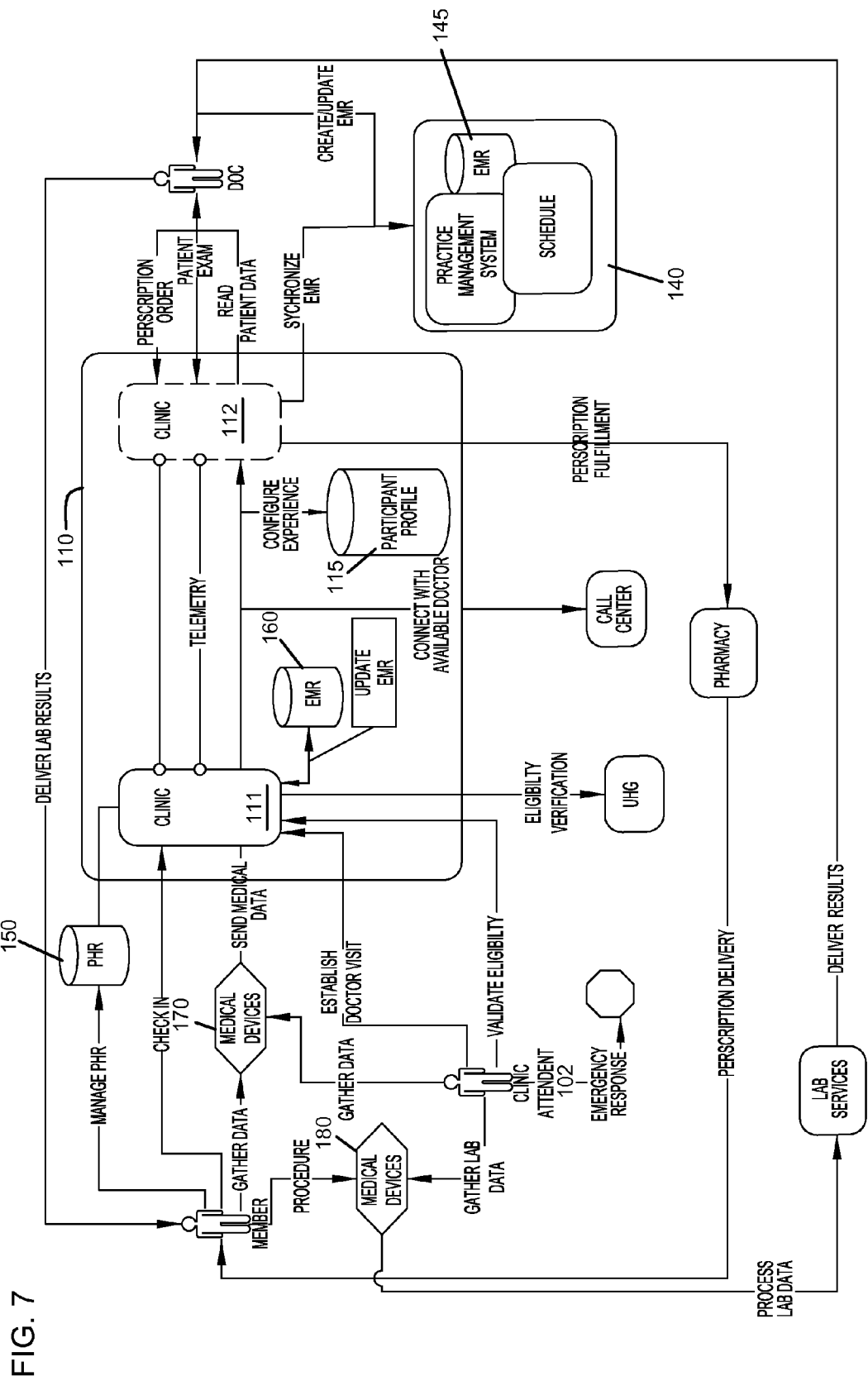
FIG. 7 illustrates additional business components that may be associated with the telehealth communications network.

Customer EMRs may be simple or comprehensive and may include some or all available customer medical information disclosed by customer and/or discovered via collecting existing medical records. FIG. 7 illustrates business components that may be useful sources of data for storage in a customer's EMR. Each of the business components depicted in FIG. 7 may be a part of, or may be associated with the telehealth communications network 110. For example, EMRs may be stored on an electronic medical record (EMR) database 160 located on the telehealth communications network 110. Audio and video recordings of a customer's appointment gathered from clinic 111 and provider facility 112 may be captured digitally, be electronically appended to the customer's EMR, and stored on EMR database 160. Furthermore, additional customer data may be captured related to an appointment including activities performed by parties to the appointment during the appointment. For example, medical imagery, digital telemetry, and diagnostic test readings taken in real-time from in-clinic systems may be collected by medical devices 170 coupled to the telehealth communications network and stored in a customer's EMR. Furthermore, lab work data 180 or non-digital diagnostic tests and telemetry (weight, blood pressure, glucose, height, etc.) data from devices not coupled to the telehealth communication network may be entered into a customer's EMR residing on EMR database 160 by a clinic attendant 102 using software coupled to the telehealth communications network 110 within clinic 111. In addition, information related to additional appointments, referrals, tests, and prescriptions may be captured. Furthermore, data for a customer's EMR may be received from sources such as other telehealth communication networks, other insurers, and/or a customer's personal health record.

EMRs may be made available to parties scheduled for an appointment at the permission of the customer. In some implementations, a customer's participant profile stored on participant profile database 115 may dictate which party has access to the customer's EMR. Thus, all or a portion of a customer's consolidated medical record may be accessible via the telehealth communications network via a secure web interface per customer's instructions for sharing medical records in compliance with HIPAA guidelines and including customer acceptance of sharing. For example, a customer may decide whether all or a portion of their electronic medical record may be accessed and stored at provider portal 140 in an EMR database 145, i.e., a customer may decide whether a doctor's office may store, view and/or share the customer's medical information. Furthermore, in certain implementations, a customer may access a personal health record database 150 via a web interface where the customer may access and manage, e.g., edit, their health record.

After an appointment, a customer's EMIR may be updated, any existing EMRs on the network may be synchronized, and the EMR may be stored in a repository. By providing an updated EMR for a provider to review, a customer may be more easily diagnosed and treated. Furthermore, updated EMRs may facilitate prescribing medication for the customer, and medications may be electronically prescribed using the telehealth communications network 110.

As discussed above, providing data entry, receiving and storage means enables users of the telehealth communications network 110 to create, store and edit profiles for providers. Accordingly, data related to a provider's practice, specialty, clinic/business location, proximity to customer clinics, proximity to hospitals near customer clinics, cost, gender, affiliation, spoken language, and/or physician/hospital quality ranking may be entered, stored, and edited using the telehealth communications network 110. The provider profile information may be accessed or retrieved by the centralized scheduling system in order to match customers with providers based on a customer's requests or data within a customer's electronic medical record. Furthermore, all or a portion of a provider's profile may be accessed by a customer via customer portal 130. For example, while a customer accesses customer portal 130 to schedule an appointment using scheduling tool 120, the customer may review provider profiles to identify a provider that matches their preferences and then proceed to schedule an appointment with their preferred provider.

Figure 8:
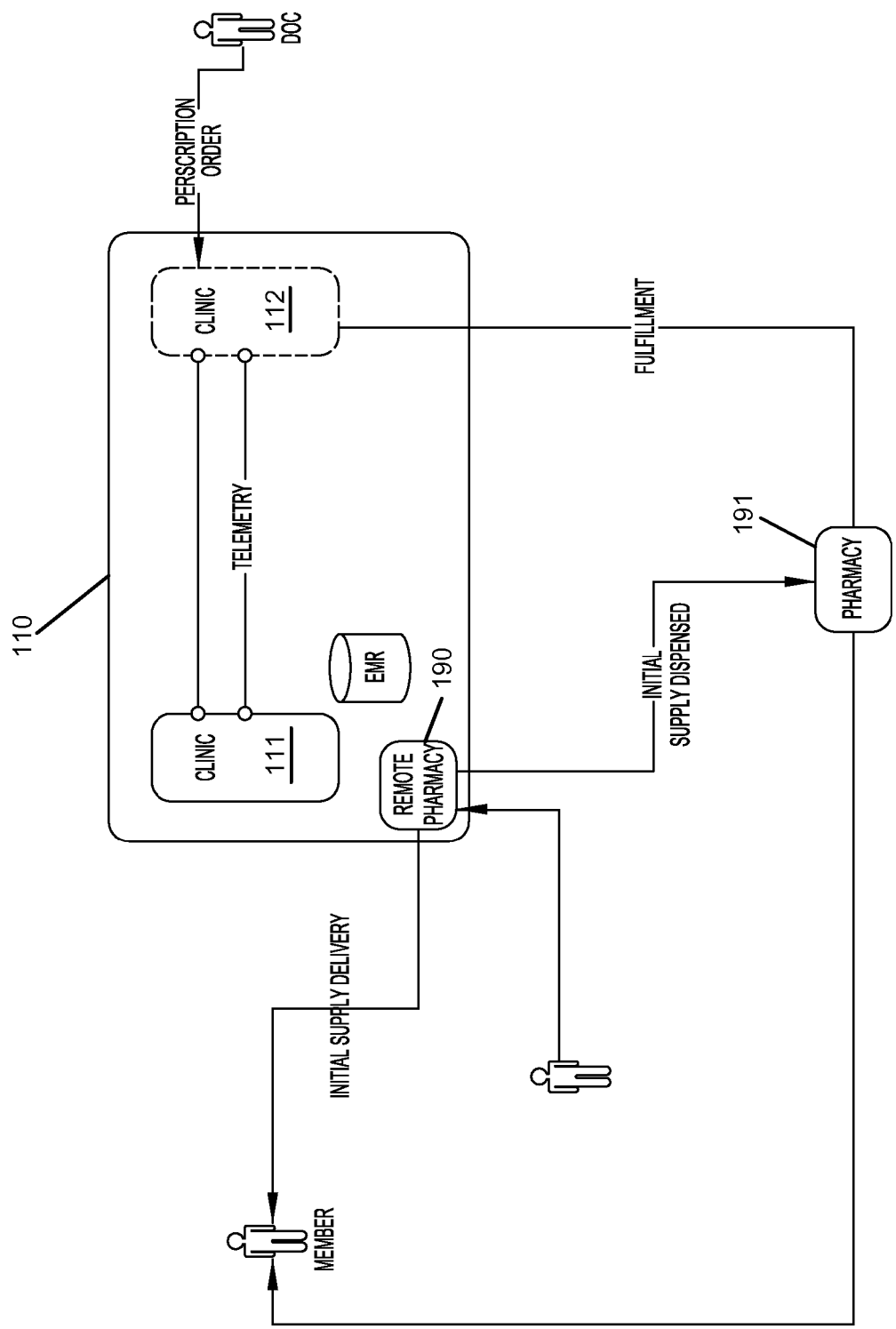
FIG. 8 illustrates the kiosk and pharmacy components of the telehealth communications network for providing prescription integration.

FIG. 8 illustrates the kiosk and pharmacy components of the telehealth communications network for providing prescription integration. In some implementations, an electronic prescription may be generated and transmitted over the telehealth communications network 110, which may be integrated with an authorized provider's software that documents the prescription information, confirms the availability of drugs in the clinic kiosk 190, dispenses an initial supply of medications, and sends a prescription for the remaining drugs to the pharmacy 191 of a customer's choice. Clinics may have small supplies of the most commonly prescribed drugs available for immediate treatment needs which are delivered via on-site kiosk 190. Complete customer prescriptions may be filled electronically and available via mail or at a pharmacy 191 of choice.

Figure 9:
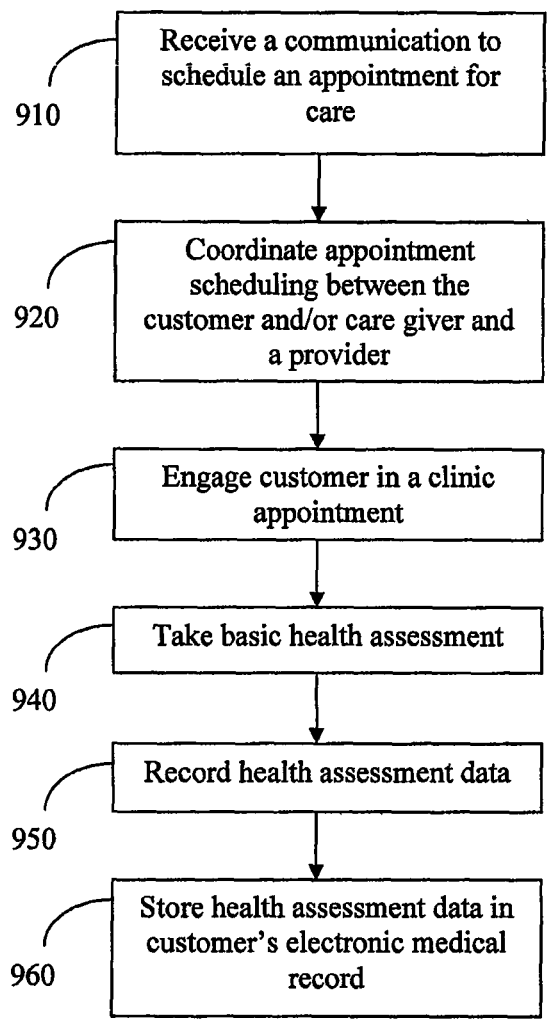
FIG. 9 provides a flowchart of the operation of the telehealth communications network.
Figure 10:
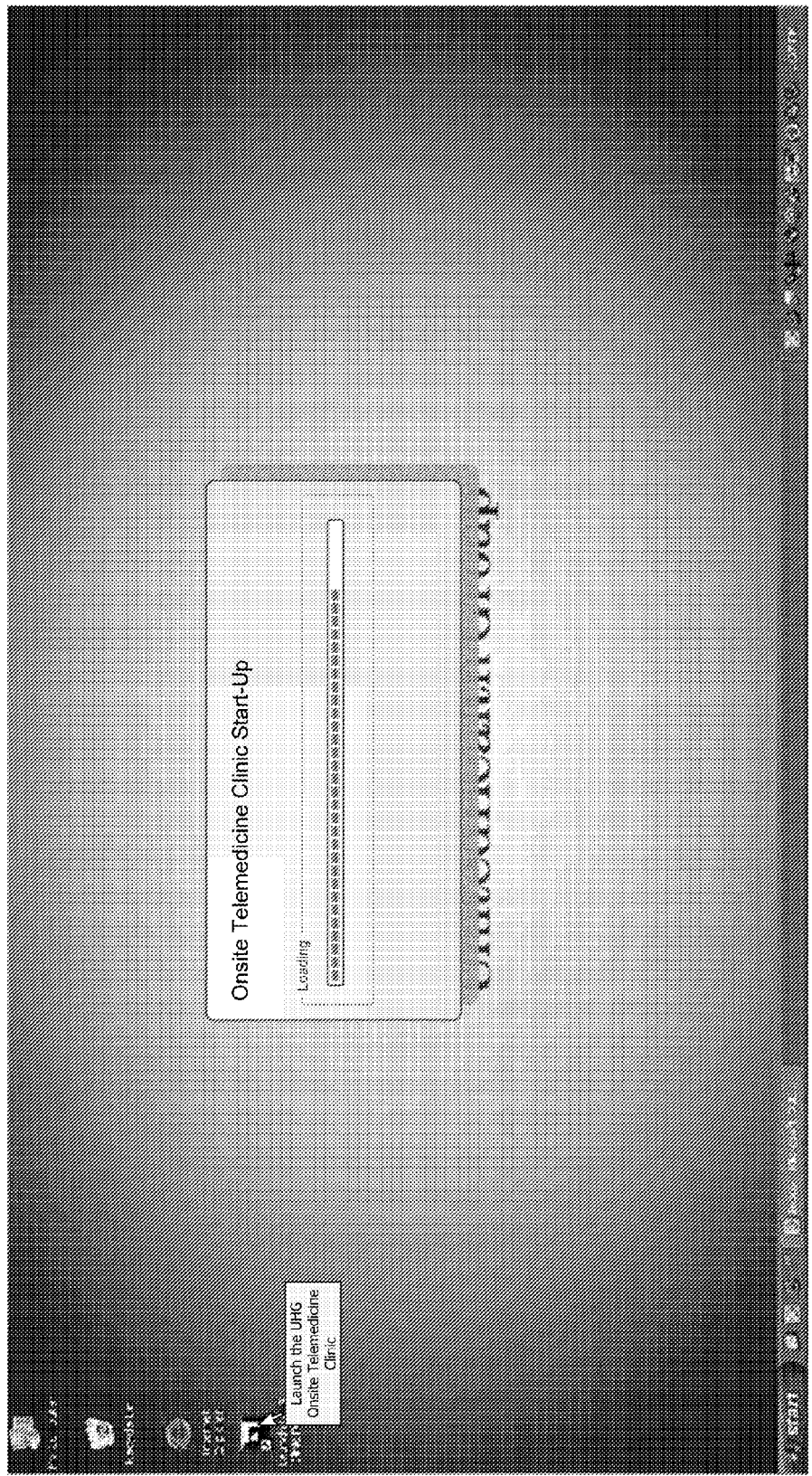
Figure 11:
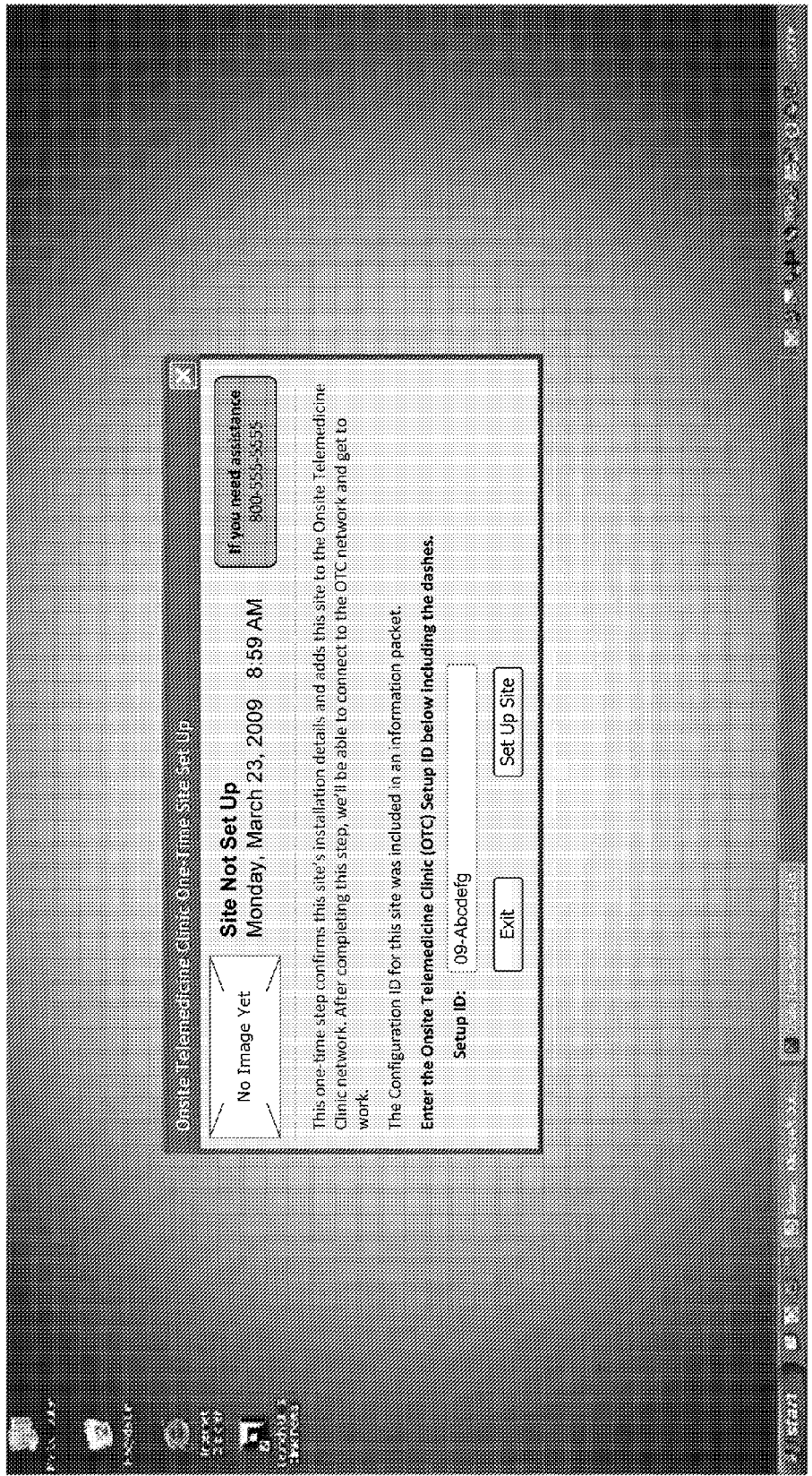
Figure 12:
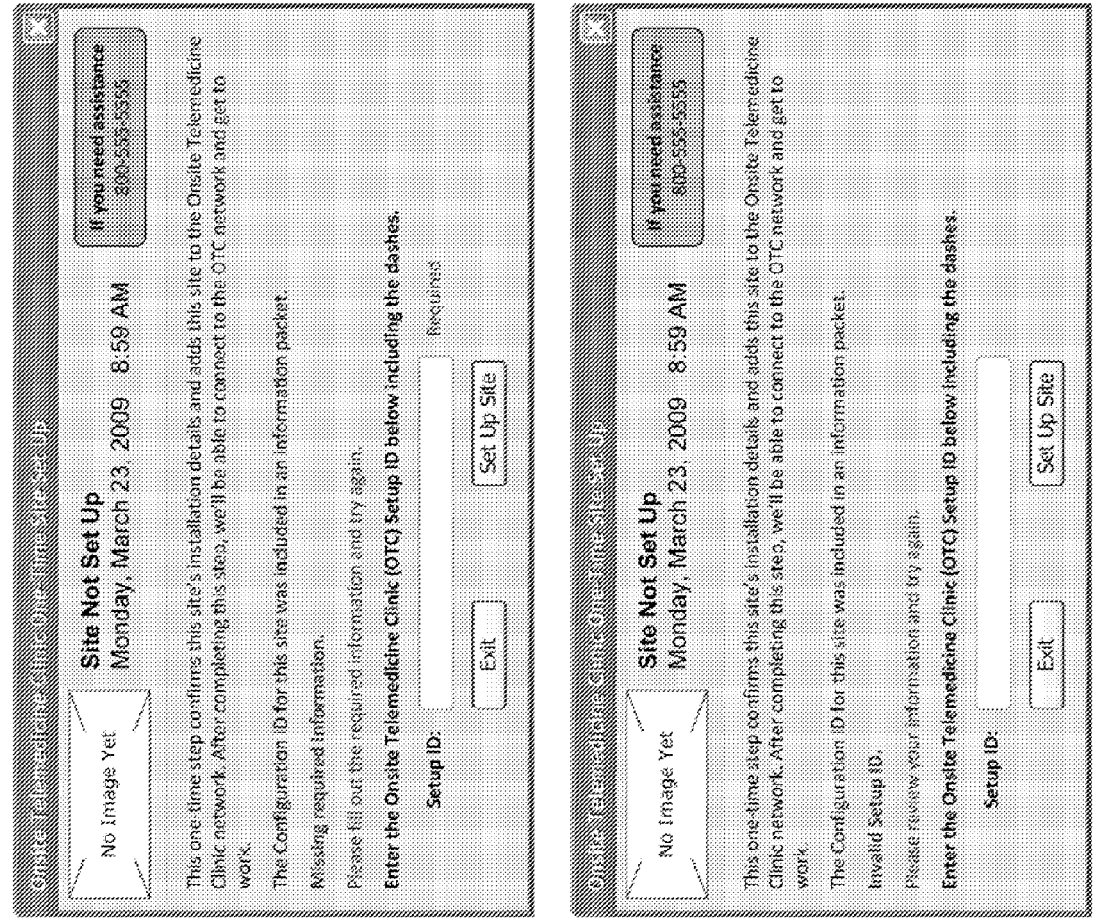
Figure 13:
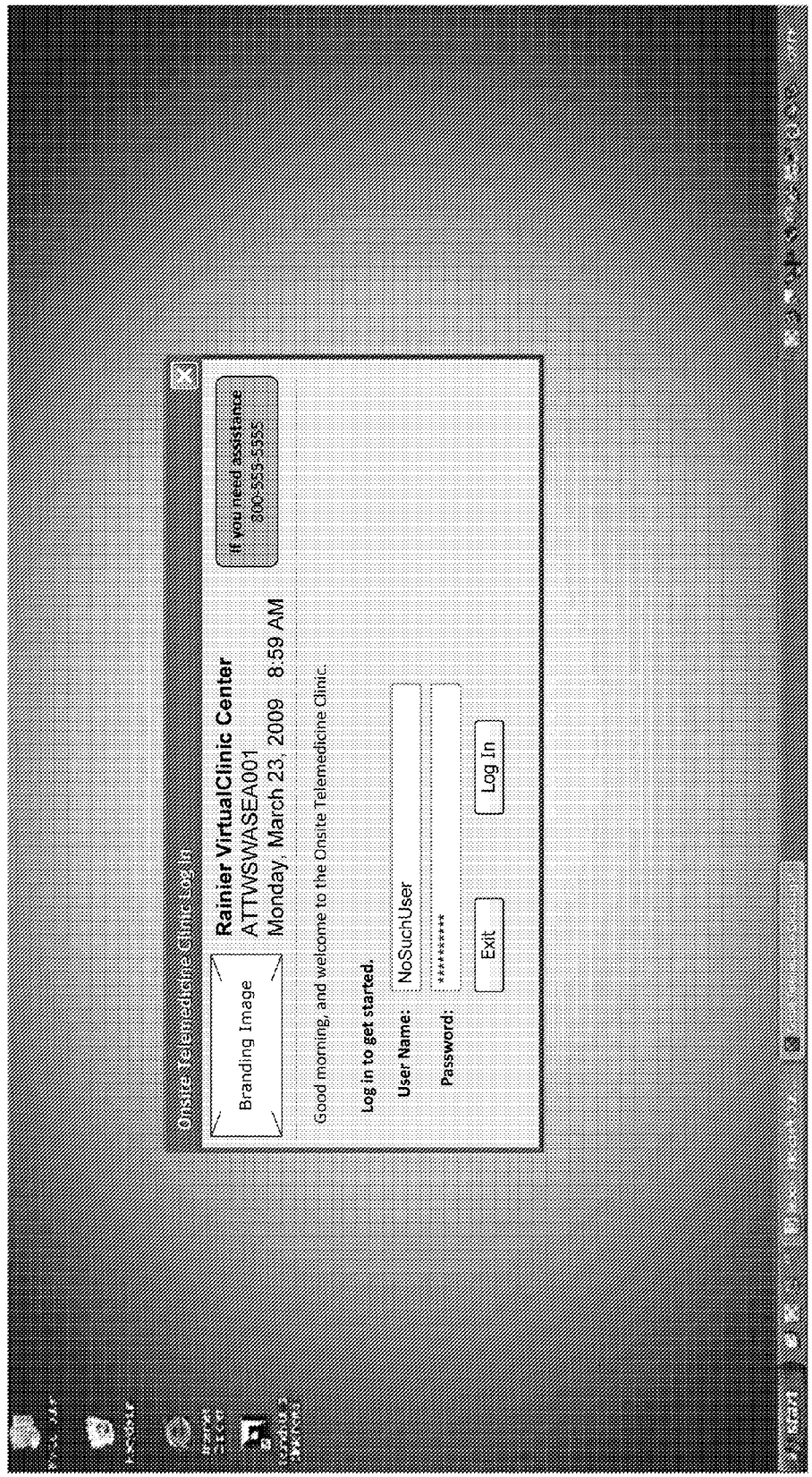
Figure 15:
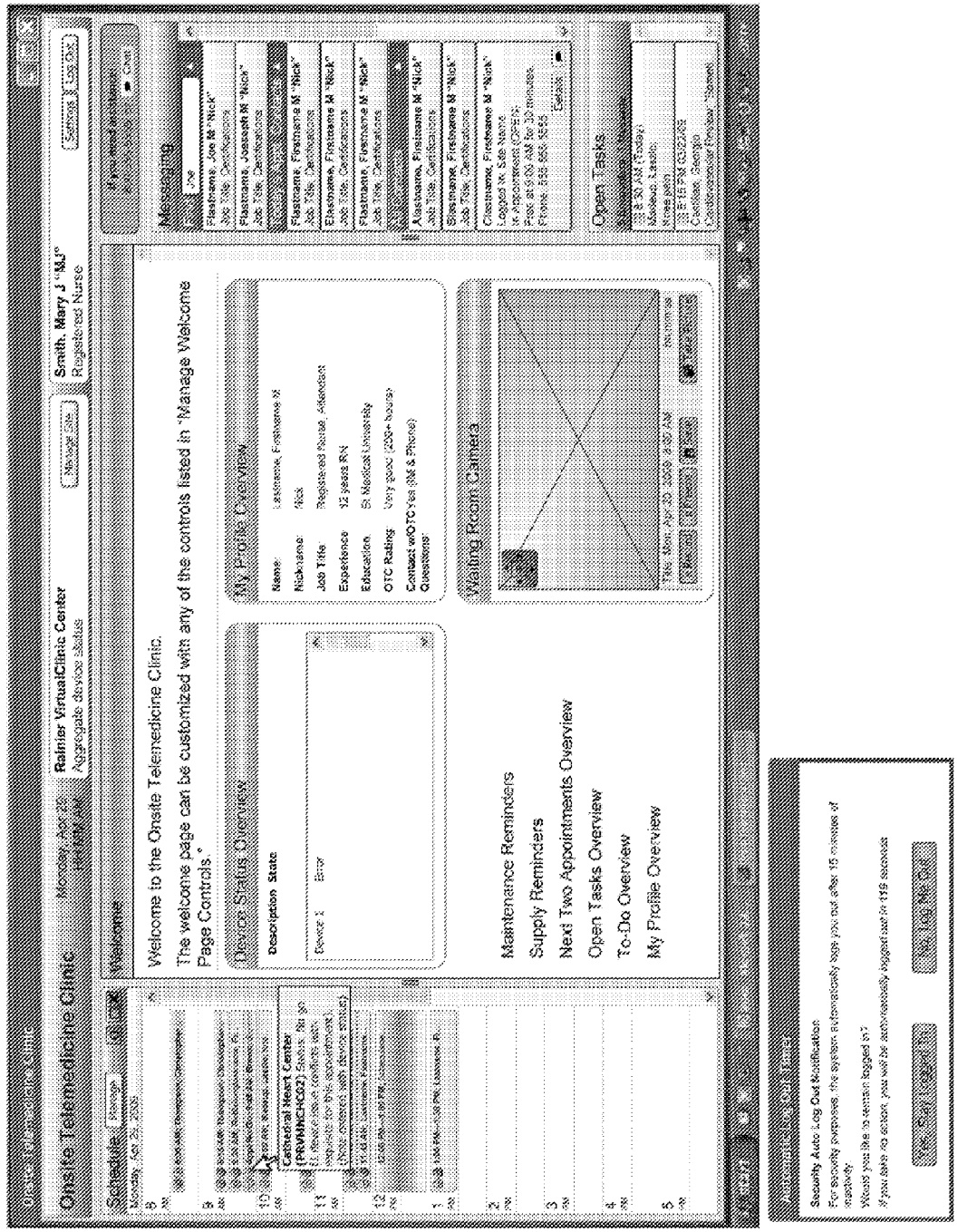
Figure 16:
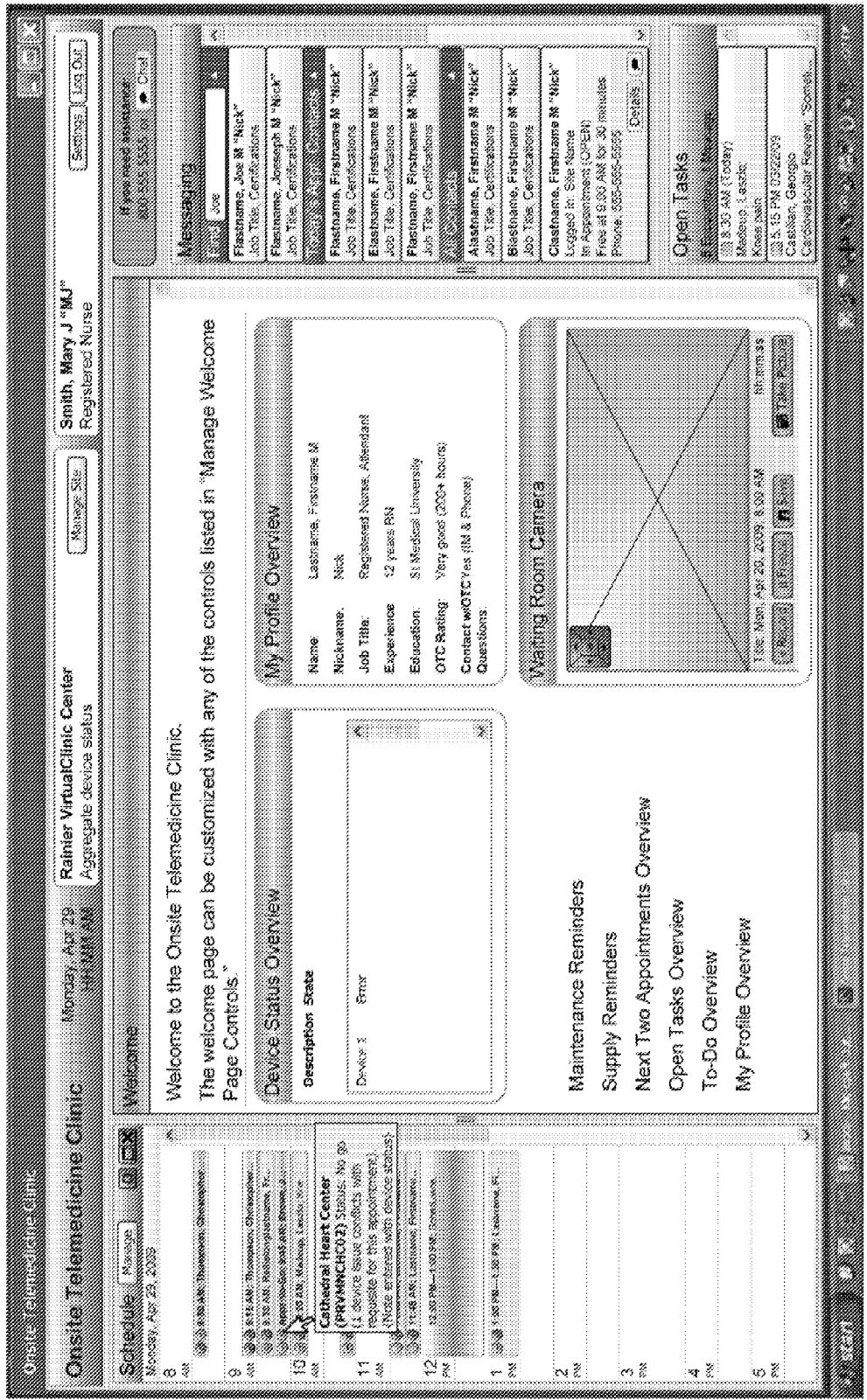

FIG. 9 provides a flowchart of a method (900) of operation of the telehealth communications network. According to one embodiment, the telehealth communications network receives (910) a communication, e.g., via a customer portal, indicating a customer desires to schedule an appointment (or requests assistance in scheduling multiple provider and/or caregiver appointments) for care. In some implementations, scheduling the appointment may involve describing the customer's symptoms.

An appointment between a customer and a provider is coordinated (920), e.g., via scheduling software, which may include matching the customer's needs based on their symptoms with the appropriate point-of-care site. For example, where a customer's symptoms includes itchy, red eyes, a point-of-care site equipped with an ophthalmic scope may be reserved. Where a customer's symptoms includes a skin rash, a point-of-care site with a dermascope may be reserved. Alternatively, once an appointment is scheduled for a particular point-of-care site, the site may be outfitted with required and optional equipment prior to conducting the examination. Of course, the telehealth communications network may be used to promote preventative medicine, increase customer engagement and to triage care appropriately. For example, a diabetic patient may visit a telehealth communications network point-of-care site in order to have their eyes and feet examined by a remotely located physician or diabetes specialist in order to prevent damage to the retina or foot abnormalities associated with diabetes.

A customer is engaged (930) with the telehealth communications network when the customer visits the point-of-care site, which may be a publicly accessible, private and secure environment. The customer engagement may be an examination session, which may include diagnosis, follow-up, general questions, education, second opinions, consultations with other specialists, case management, prescriptions, standard diagnostic tests, and any tests from which digital information can be transferred. During a customer's visit, a basic health assessment is taken (940) that may include a survey along with height, weight, and blood pressure measurements.

The customer's health assessment data is recorded (950) via computer entry and is available to the customer and provider(s) electronically via the telehealth communications network.

Upon completion of the session, customer information may be electronically stored (960) to the customer's health record or the physician's EMR. In addition, any follow-up appointments may be scheduled, prescriptions may be filled, and treatment outcomes may be recorded via the telehealth communications network.

The operation of the telehealth communications network may include various additions or modifications. For example, health assessment data may be stored centrally and remotely in secure servers operated by a health insurance provider. According to certain embodiments, the telehealth communications network 110, along with its central scheduling system, may be controlled by a health insurance provider. According to this example, a health insurance provider may engage any of a variety of providers to participate in the telehealth communications network 110, and may establish any number of clinics for providing customers access to the remotely located providers. This allows the telehealth network to offer customers proximately located to a clinic with remote access to nearly any type of provider and thus nearly any type of medical consultation, e.g., ranging from general medical advice to advice related to specialized medicine. Accordingly, a customer that may not otherwise have access to healthcare may travel to a proximately located clinic and be examined by a qualified, remotely located provider and may receive diagnosis and treatment advice. Furthermore, a health insurance provider-controlled telehealth communications network may provide built-in methods of confirming whether a customer's insurance plan covers an appointment with a particular provider or a particular type of provider. In addition, other aspects of administering insurance may be streamlined due to the access the insurance provider has to the telehealth scheduling and communications network.

In another example, audio and video equipment can be made mobile utilizing satellite or other telecommunication methods to take the clinic to the customer or to a location accessible to the customer.

According to some embodiments, customer-provider sessions may be facilitated by a primary physician or a clinic nurse present at the customer's location.

In certain implementations, payment processing for providers requiring payment for services delivered during an appointment may be performed by digitally confirming online billing codes and payment terms as part of the scheduling process and prior to the appointment via the telehealth communications network. This may allow electronic billing processing to occur shortly after the appointment is held.

Although the present invention has been described with reference to preferred embodiments, persons skilled in the art will recognize that changes may be made in form and detail without departing from the spirit and scope of the invention.

What is claimed is:

1. A telehealth communications network accessible over the Internet for facilitating a medical encounter between a patient at a patient site and a provider at a provider site remotely located from the patient, the telehealth communications network comprising:

an operating console comprising at least one memory and at least one processor coupled to the network, the operating console configured to execute a plurality of workflows, the plurality of workflows comprising a series of graphical user interfaces;

wherein the workflows are instantiated based on a type of a user, the type of user determined based on an originating Internet protocol ("IP") address and whether the IP address is associated with the patient site or the provider site;

wherein one series of graphical user interfaces are configured to be viewable by the patient at the patient site and another series of the graphical user interfaces are configured to be viewable by the provider at the provider site remotely located from the patient, the graphical user interfaces for facilitating and guiding interactions between the patient and the provider during the medical encounter; and wherein the network is configured to command medical devices and network components coupled thereto, and at least one of the graphical user interfaces at the patient site is configured to be displayed simultaneously with a graphical user interface at the provider site and each comprises at least one image that guides use of at least one of the medical devices at the patient site.

2. The telehealth communications network of claim 1, further comprising a platform communicatively coupled to the operating console for providing an interface to operate the medical devices and the network components.

3. The telehealth communications network of claim 2, further comprising a clinic workstation for supporting the computational needs of the patient site and the provider site, wherein the clinic workstation comprises a device adaptor aggregator for communicatively coupling the medical devices.

4. The telehealth communications network of claim 1, further comprising a unified communication console configured to present data to the patient and the provider and to enable interactions between devices at the patient site and at the provider site.

5. The telehealth communications network of claim 4, wherein the unified communication console comprises a conference engine interface for managing a video conferencing connection.

6. The telehealth communications network of claim 4, wherein the unified communication console is communicatively coupled to a telemetry display for displaying telemetry data and for providing a user interface enabling the patient and provider to interact with the telemetry display settings and output.

7. The telehealth communications network of claim 6, further comprising a telemetry control for coupling the telemetry display to the medical devices.

8. The telehealth communications network of claim 7, further comprising a telemetry adaptor for managing the medical devices and the integration of the medical devices to the network.

9. The telehealth communications network of claim 1, further comprising a centralized scheduling system comprising:
   a clinic tool for storing and updating at least one clinic schedule;
   a provider tool for storing and updating a provider schedule at a provider clinic and a provider profile;
   a customer tool for receiving an appointment request from a customer and providing the customer with an available appointment for the at least one clinic based on the appointment request, said available appointment identified by the scheduling tool by matching the appointment request with data associated with at least one of the clinic schedule, provider schedule and provider profile; and
   wherein during a time corresponding to a customer accepted available appointment, the customer located at one of the at least one clinic interacts with a provider remotely located at the provider facility.

10. The network of claim 1, wherein the plurality of workflows comprises a workflow configured to verify patient utilization at the patient site based on bandwidth use.

11. A computer-implemented method for implementing a plurality of workflows across the Internet, the plurality of workflows stored in memory and implemented by a computer processor within a network, the plurality of workflows comprising the steps of:
   providing a user access to the network based on the role of the user, wherein the role of the user is one of a patient or a physician;
   controlling the transmission and receipt of data across the multi-site medical network in response to workflow processes engaged in by the user; and
   guiding the user through at least one of a clinical and a business process for facilitating communications with other network users located remotely from the user;
   wherein the plurality of workflows are instantiated based on the role of the user, the role of the user determined based on an Internet protocol ("IP") address and whether the IP address is associated with a patient site or a physician site;
   wherein the plurality of workflows comprises a series of graphical user interfaces, such that one series of graphical user interfaces is configured to be viewable by a patient at the patient site and another series of graphical user interfaces is configured to be viewable by a physician at the physician site remotely situated from the patient during a medical encounter, the graphical user interfaces configured to facilitate and guide interactions between the patient and the physician; and
   wherein at least one of the graphical user interfaces at the patient site is configured to be displayed simultaneously with at least one of the graphical user interfaces at the physician site and each comprises at least one image that guides use of at least one medical device at the patient site; and
   wherein the steps of providing, controlling and guiding are performed by the computer processor.

12. The computer-implemented method of claim 11, wherein the plurality of workflows comprises a patient check-in workflow and wherein the user is a patient, the patient check-in workflow allowing the patient to provide authorization for one or more of accessing records or receipt of treatment.

13. The computer-implemented method of claim 11, wherein the plurality of workflows comprises a patient encounter workflow and wherein the user is at least one of the physician or an attendant, the patient encounter workflow providing access to patient health information.

14. The computer-implemented method of claim 11 wherein the plurality of workflows comprises a workflow configured to verify patient utilization at the patient site based on bandwidth use.

* * * * *

UNITED STATES PATENT AND TRADEMARK OFFICE
CERTIFICATE OF CORRECTION

PATENT NO.         : 8,799,010 B2
APPLICATION NO.    : 12/437479
DATED              : August 5, 2014
INVENTOR(S)        : Murali P. Kaundinya et al.

It is certified that error appears in the above-identified patent and that said Letters Patent is hereby corrected as shown below:

Specification

| Column | Line | PTO | Should Be |
|---|---|---|---|
| 2 | 12 | "proactively scheduled, appointment" | —proactively scheduled appointment— |
| 11 | 13 | "record (EMIR) available" | —record (EMR) available— |
| 16 | 38 | "a customer's EMIR may" | —a customer's EMR may— |

Signed and Sealed this
Eleventh Day of November, 2014

Michelle K. Lee
*Deputy Director of the United States Patent and Trademark Office*